United States Patent
Uckun et al.

(10) Patent No.: US 6,528,495 B1
(45) Date of Patent: Mar. 4, 2003

(54) ARYL PHOSPHATE DERIVATIVES OF D4T HAVING ANTI-HIV ACTIVITY

(75) Inventors: Fatih M. Uckun, White Bear Lake, MN (US); Rakesh Vig, Little Canada, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/548,492

(22) Filed: Apr. 13, 2000

Related U.S. Application Data

(63) Continuation of application No. 09/464,516, filed on Dec. 15, 1999, which is a continuation of application No. 09/107,716, filed on Jun. 30, 1998.

(51) Int. Cl.$^7$ ................... C07H 19/073; A61K 31/70; A61K 31/17

(52) U.S. Cl. .................. 514/51; 514/49; 514/50; 536/26.1; 536/26.8; 536/28.2

(58) Field of Search ............... 514/51, 49, 50; 536/26.1, 26.8

(56) References Cited

U.S. PATENT DOCUMENTS

| | | |
|---|---|---|
| 4,707,362 A | 11/1987 | Nuwayser |
| 4,841,039 A | 6/1989 | Chu et al. |
| 5,069,906 A | 12/1991 | Cohen et al. |
| 5,595,980 A | 1/1997 | Brode et al. |
| 5,659,023 A | 8/1997 | Alexander et al. |
| 5,672,698 A | 9/1997 | Chen et al. |
| 5,750,729 A | 5/1998 | Alexander et al. |

FOREIGN PATENT DOCUMENTS

| | | |
|---|---|---|
| JP | 6189998 | 7/1994 |
| WO | WO 94/14831 | 7/1994 |
| WO | WO 96/29336 | 9/1996 |
| WO | WO 97/42962 | 11/1997 |

OTHER PUBLICATIONS

Alexander, P. et al., "Synthesis and Antiviral Activity of Pyranosylphosphonic Acid Nucleotide Analogues", *J. Med. Chem.*, 39:1321–1330 (Mar. 15, 1996).

Balzarini, J. et al, "Differential Patterns of Intracellular Metabolism of 2', 3'–Didehydro–2', 3'–dideoxythymidine and 3'–Azido–2', 3'–dideoxythymidine, Two Potent Anti–human Immunodeficiency Virus Compounds", *J. Biol. Chem.*, 264(11):6127–6133 (Apr. 15, 1989).

Bourinbaiar, A. et al., "Anti–HIV Effect of Gramicidin in Vitro: Potential for Spermicide Use", *Life Sciences*, 54(1):PL5–9 (1994).

Bourinbaiar, A. et al., "Comparative in vitro Study of Contraceptive Agents with Anti–HIV Activity: Gramicidin, nonoxynol–9, and gossypol", *Contraception*, 49(2):131–137 (Feb. 1994).

Burkman, L., "Discrimination Between Nonhyperactivated and Classical Hyperactivated Motility Patterns in Human Spermatozoa Using Computerized Analysis", *Fertility and Sterility*, 55(2):363–371 (Feb. 1991).

D'Cruz, O.J. et al., "Aryl Phosphate Derivatives of Bromo–Methoxy–Azidothymidine Are Dual–Function Spermicides with Potent Anti–Human Immunodeficiency Virus", *Biology of Reproduction*, vol. 59, pp. 503–515 (1998).

D'Cruz, O. et al., "$\beta_2$–Integrin (CD11b/CD18) Is the Primary Adhesive Glycoprotein Complex Involved in Neutrophil–Mediated Immune Injury to Human Sperm", *Biology of Reproduction*, 53(5):1118–1130 (Nov. 1995).

D'Cruz, O. et al., "Spermicidal Activity of Metallocene Complexes Containing Vanadium (IV) in Humans", *Biology of Reproduction*, 58(6):1515–1526 (Jun. 1998).

Dicker, D. et al., "The Value of Repeat Hysteroscopic Evaluation in Patients with Failed in Vitro Fertilization Transfer Cycles", *Fertility and Sterility*, 58(4):833–835 (Oct. 1992).

Erice, A. et al., "Anti–Human Immunodeficiency Virus Type 1 Activity of an Anti–CD4 Immunoconjugate Containing Pokeweed Antiviral Protein", *Antimicrobial Agents and Chemotherapy*, 37(4):835–838 (Apr. 1993).

Erlandsen, S. et al., "Membrane Fixation for High–Resolution Low–Voltage SEM: Studies on Giardia, Rat Spermatozoa, and Mouse Macrophages", *Scanning*, 11(4) 169–175 (Jul./Aug. 1989).

Furman, P. et al, "Phosphorylation of 3'–azido–3'–deoxythymidine and selective interaction of the 5'–triphosphate with Human Immunodeficiency Virus Reverse Transcriptase", *Proc. Natl. Acad. Sci. USA*, vol. 83, pp. 8333–8337 (Nov. 1986).

Hao, Z. et al., "Factors Determining the Activity of 2', 3'–Dideoxynucleosides in Suppressing Human Immunodeficiency Virus In Vitro", *Molecular Pharmacology*, 34(4):431–435 (Oct. 1988).

Jan, S.T., et al., "Synthesis of dual function (5R,6R)– and (5S,6S)–5–bromo–6–methoxy–5, 6–dihydro–AZT–5'–(para–bromophenyl methoxyalaninyl phosphate) as novel spermicidal and anti–HIV agents", *Antiviral Chemistry & Chemotherapy*, vol. 10, pp. 39–46 (Jul. 9, 1999).

(List continued on next page.)

*Primary Examiner*—Samuel Barts
*Assistant Examiner*—Howard V. Owens
(74) *Attorney, Agent, or Firm*—Merchant & Gould P.C.

(57) ABSTRACT

Aryl phosphate derivatives of d4T with para-bromo substitution on the aryl group show markedly increased potency as anti-HIV agents without undesirable levels of cytotoxic activity. In particular, these derivatives are potent inhibitors of HIV reverse transcriptase. In a preferred aspect of the present invention, the phosphorus of the aryl phosphate group is further substituted with an amino acid residue that may be esterified or substituted, such as a methoxy alaninyl group.

19 Claims, 7 Drawing Sheets

OTHER PUBLICATIONS

Jan, Shyi–Tai et al., "AZT–5'–(p–bromophenyl methoxy-alaninyl phosphate) as apotent and non–toxic anti–human immunodeficiency virus agent", *International Medical Press*, pp. 47–52 (1999).

Kumar, R. et al., "Synthesis, In Vitro Biological Stability, and Anti–HIV Activity of 5–Halo–6–alkoxy (or azido)–5, 6–dihydro–3'–azido–3'–deoxythymidine Diastereomers as Potential Prodrugs to 3'–Azido–3'–deoxythymidine (AZT)", *J. Med. Chem.*, 37(25):4297–4306 (Dec. 9, 1994).

Mansuri, M. et al., "1–(2, 3–Dideoxy–β–D–glycero–pent–2–enofuranosyl) Thymine. A highly Potent and Selective Anti–HIV Agent", *J. Med. Chem.*, 32(2):461–466 (Feb. 1989).

McGuigan, C. et al., "Aryl Phosphate Derivatives of AZT Inhibit HIV Replication in Cells Where the Nucleoside is Poorly Active", *Bioorganic & Medicinal Chemistry Letters*, 2(7):701–704 (1992).

McGuigan, C. et al., "Aryl Phosphate Derivatives of AZT Retain Activity Against HIV1 in Cell Lines Which are Resistant to the Action of AZT", *Antiviral Research*, 17(4):311–321 (Apr. 1, 1992).

McGuigan, C. et al., "Aryl Phosphoramidate Derivatives of d4T Have Improved Anti–HIV Efficacy in Tissue Culture and May Act by the Generation of a Novel Intracellular Metabolite", *J. Med. Chem.*, 39(8):1748–1753 (Apr. 12, 1996).

McGuigan, C. et al., "Intracellular Delivery of Bioactive AZT Nucleotides by Aryl Phosphate Derivatives of AZT", *J. Med. Chem.*, 36(8):1048–1052 (Apr. 16, 1993).

McGuigan, C. et al., "Phosphoramidates as Potent Prodrugs of Anti–HIV Nucleotides: Studies in the Amino Region", *Antiviral Chemistry & Chemotherapy*, 7(1):31–36 (1996).

McGuigan, C. et al., "Phosphoramidate Derivatives of AZT as Inhibitors of HIV: Studies on the Carboxyl Terminus", *Antiviral Chemistry & Chemotherapy*, 4(2):97–101 (1993).

McGuigan, C. et al., "Phosphoramidate Derivatives of d4T with Improved Anti–HIV Efficacy Retain Full Activity in Thymidine Kinase–Deficient Cells", *Bioorganic & Medicinal Chemistry Letters*, 6(10):1183–1186 (May 21, 1996).

McIntee, E. et al., "Probing the Mechanism of Action and Decomposition of Amino Acid Phosphomonoester Amidates of Antiviral Nucleoside Prodrugs", *J. Med. Chem.*, 40(21):3323–3331 (Oct. 10, 1997).

Niruthisard, S. et al., "The Effects of Frequent Nonoxynol–9 Use on the Vaginal and Cervical Mucosa", *Sexually Transmitted Diseases*, 18(3):176–179 (Jul.–Sep. 1991).

Siddiqui, A. et al., "Design and Synthesis of Lipophilic Phosphoramidate d4T–MP Prodrugs Expressing High Potency Against HIV in Cell Structure: Structural Determinants for in Vitro Activity and QSAR".

Siddiqui, A. et al., "The Presence of Substituents on the Aryl Moiety of the Aryl Phosphoramidate Derivatives of d4T Enhances Anti–HIV Efficacy in Cell Culture: A Structure–Activity Relationship", *J. Med. Chem.*, 42:393–399 (1999).

Stoffel, M. et al., "Improved Preservation of Rat Epididymal Sperm for High–Resolution Low–Voltage Scanning Electron Microscopy (HR–LVSEM)", *Molecular Reproduction and Development*, 34(2):172–182 (Feb. 1993).

Tryphonas, L. et al., "Morphologic Evidence for Vaginal Toxicity of Delfen Contraceptive Cream in the Rat", *Toxicology Letters*, 20(3):289–295 (Mar. 1984).

Uckun, F. et al., "TXU (Anti–CD7)–Pokeweed Antiviral Protein as a Potent Inhibitor of Human Immunodeficiency Virus", *Antimicrobial Agents & Chemotherapy*, 42(2):383–388 (Feb. 1998).

Venkatachalam, T. K. et al., "Enhancing Effects of a Mono–Bromo Substitution at the Para Position of the Phenyl Moiety on the Metabolism and Anti–HIV Activity of D4T–Phenyl Methoxyalaninyl Phosphate Derivatives", *Bioorganic & Medicinal Chemistry Letters*, pp. 3121–3126 (1998).

Vig, R. et al., "Aryl phosphate derivatives of 3'–deoxythymidine are not potent anti–human immunodeficiency virus agents", *International Medical Press*, pp. 439–443 (1998).

Vig, R. et al., "D4T—5'[p–Bromophenyl Methoxyalaninyl Phosphate] as a Potent and Non–Toxic Anti–Human Immunodeficiency Virus Agent", *Antiviral Chem. Chemother.*, vol. 9(5), pp. 445–448 (1998).

Wang, L. et al., "In Vivo Biodistribution, Pharmacokinetic Parameters, and Brain Uptake of 5'–Halo–6–methory (or ethoxy)–5, 6–dihydro–3'–azido–3'–deoxythymidine Diastereomers as Potential Prodrugs of 3'–Azido–3'–deoxythymidine", *J. Med. Chem.*, 39(4):826–833 (Feb. 16, 1996).

Wiebe, L. et al., "5–Halo–6–alkoxy–5, 6–dihydro–pyrimidine Nucleosides: Antiviral Nucleosides or Nucleoside Prodrugs", *Nucleosides & Nucleotides*, 14(3–5):501–505 (May/Jun./Jul. 1995).

Wilborn, W. et al., "Scanning Electron Microscopy of Human Spermatozoa after Incubation with the Spermicide Nonoxynol–9", *Fertility and Sterility*, 39(5):717–719 (May 1983).

Zarling, J. et al., "Inhibition of HIV Replication by Pokeweed Antiviral Protein Targeted to CD4+ Cells by Monoclonal Antibodies", *Nature*, 347(6288):92–95 (Sep. 6, 1990).

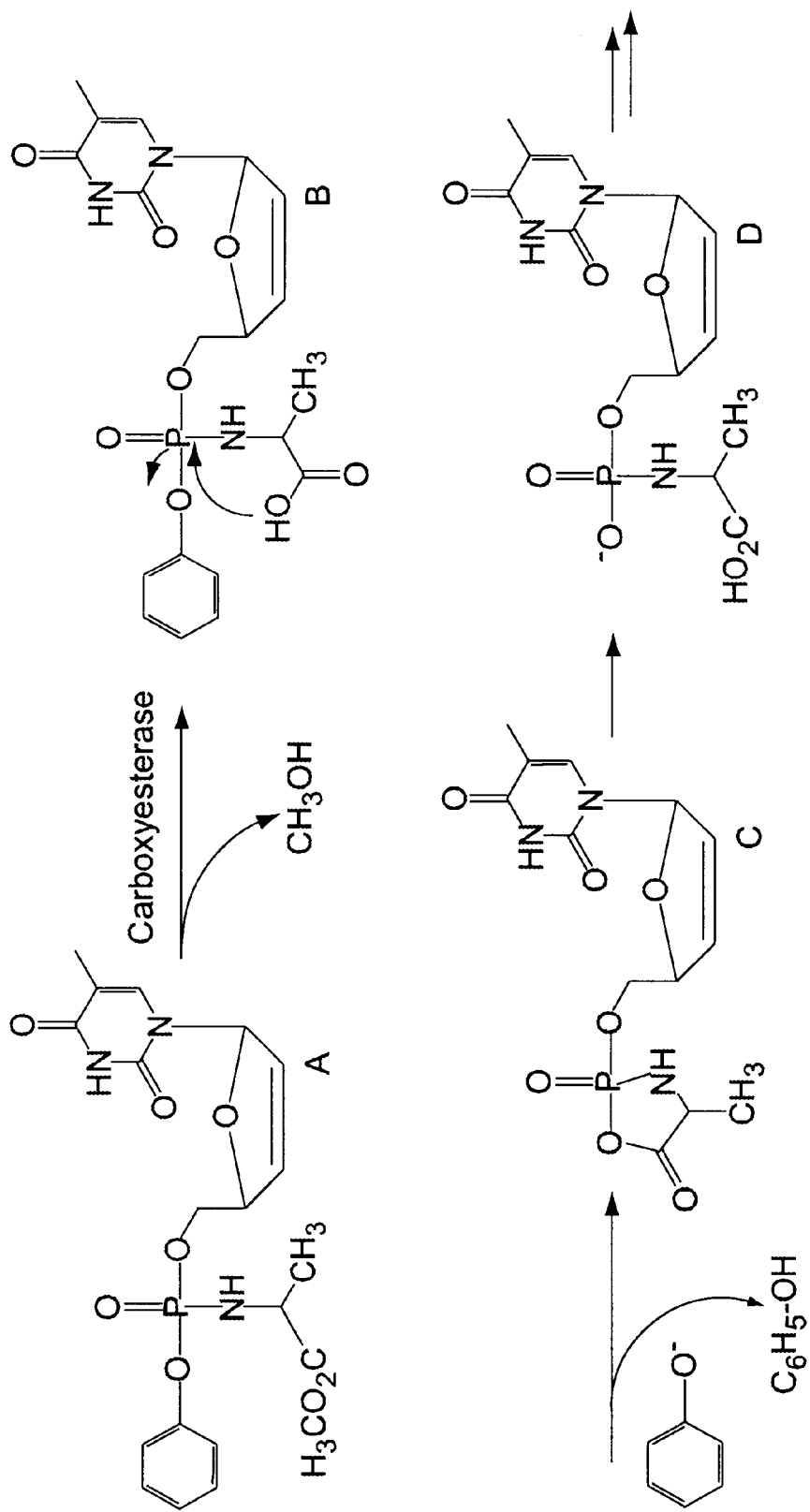
Fig. 1  Literature proposed metabolic pathway of aryl phosphate derivatives of d4T.

ARYL PHOSPHATE DERIVATIVES OF D4T HAVING ANTI-HIV ACTIVITY

This application is a Continuation of application Ser. No. 09/464,516, filed Dec. 15, 1999, which is a Continuation of application Ser. No. 09/107,716, filed Jun. 30, 1998, which applications are incorporated herein by reference.

FIELD OF THE INVENTION

The present invention is directed to aryl phosphate derivatives of 2',3'-didehydro-2',3'-dideoxythymidine (hereinafter "d4T") that exhibit potent activity against the human immune deficiency virus (HIV), e.g. as inhibitors of HIV reverse transcriptase.

BACKGROUND OF THE INVENTION

The spread of AIDS and the ongoing efforts to control the responsible virus are well-documented. One way to control HIV is to inhibit its reverse transcriptase activity (RT). Thus, novel, potent, and selective inhibitors of HIV RT are needed as useful therapeutic agents. Known, potent inhibitors of HIV RT include 5'-triphosphates of 2',3'-dideoynucleoside ("ddN") analogues. These active RT inhibitors are generated intracellularly by the action of nucleoside kinase and nucleotide kinase. Thus ddN compounds such as AZT and d4T have been considered to hold much promise in the search for anti-HIV agents.

The rate-limiting step for the conversion of 3'-azido-3'-deoxythymidine (Zidovudine; AZT) to its bioactive metabolite AZT-triphosphate seems to be the conversion of the monophosphate derivative to the diphosphate derivative, whereas the rate-limiting step for the intracellular generation of the bioactive 2',3'-dideoxy-2',3'-didehydrothymidine (d4T) metabolite d4T-triphosphate was reported to be the conversion of the nucleoside to its monophosphate derivative.(Balzarini et.al., 1989, *J.Biol. Chem.* 264:6127; McGuigan et.al., 1996, *J. Med. Chem.* 39:1748). See FIG. 1 for the mechanism proposed in the prior art.

In an attempt to overcome the dependence of ddN analogues on intracellular nucleoside kinase activation, McGuigan et al. have prepared aryl methoxyalaninyl phosphate derivatives of AZT (McGuigan et.al., 1993 *J. Med. Chem.* 36:1048; McGuigan et.al., 1992 *Antiviral Res.* 17:311) and d4T (McGuigan et.al., 1996 *J.Med..Chem.*39:1748; McGuigan et.al., 1996 *Bioorg.Med.Chem..Lett.* 6:1183). Such compounds have been shown to undergo intracellular hydrolysis to yield monophosphate derivatives that are further phosphorylated by thymidylate kinase to give the bioactive triphosphate derivatives in a thymidine kinase (TK)-independent fashion. However, all attempts to date to further improve the potency of the aryl phosphate derivatives of d4T by various substitutions of the aryl moiety without concomitantly enhancing their cytotoxicity have failed(McGuigan et.al., 1996 *J.Med.Chem.* 39:1748).

In the present invention, it has been discovered that a substitution at the phenyl moiety in the phenyl methoxyalaninyl phosphate derivative of d4T with an electron-withdrawing moiety such as a para-bromo substitution, enhances the ability of the phenyl methoxyalaninyl derivative of d4T to undergo hydrolysis due to the electron withdrawing property of the bromo substituent. The substituted phenyl phosphate derivative of d4T demonstrate potent and specific anti-viral activity.

SUMMARY OF THE INVENTION

The present invention is based on the unexpected discovery that aryl phosphate derivatives of d4T, for example having an electron-withdrawing substutution such as a para-bromo substitution on the aryl group, show markedly increased potency as anti-HIV agents without undesirable levels of cytotoxic activity. In particular, these derivatives are potent inhibitors of HIV reverse transcriptase. In a preferred aspect of the present invention, the phosphorus of the aryl phosphate group is further substituted with an amino acid residue that may be esterified or substituted such as a methoxy alaninyl group.

The para-bromo substituted phenyl methoxyalaninyl phosphate derivative of d4T as an active anti-HIV agent potently inhibits HIV replication in peripheral blood mononuclear cells (PBMNC) as well as TK-deficient CEM T-cells without any detectable cytotoxicity. Furthermore, this novel d4T derivative, d4T-5'-(para-bromophenyl methoxyalaninyl phosphate), had potent antiviral activity against RTMDR-1, an AZT- and NNI-resistant strain of HIV-1, and moderate activity against HIV-2. Similarly, the corresponding para-bromo substituted phenyl methoxyalaninyl phosphate derivative of AZT showed potent anti-HIV activity in PBMNC as well as TK-deficient CEM T-cells but it was not effective against the AZT- and NNI-resistant RTMDR-1 or HIV-2. In contrast to these d4T and AZT derivatives, the corresponding 3dT derivative, 3dT-5'-(para-bromophenyl methoxyalaninyl phosphate), showed no significant anti-HIV activity in PBMNC or TK-deficient CEM T-cells. To our knowledge, this is the first report of a previously unappreciated structure activity relationship determining the potency of phenyl phosphate derivatives of both d4T and AZT.

The lead compounds d4T-5'-(para-bromophenyl methoxyalaninyl phosphate) and AZT-5'-(para-bromophenyl methoxyalaninyl phosphate provide a basis for the design of effective HIV treatment strategies capable of inhibiting HIV replication, and particularly in TK-deficient cells.

BRIEF DESCRIPTION OF THE DRAWINGS

FIG. 1 is a schematic diagram of a prior art-proposed metabolic pathway for aryl phosphate derivatives of d4T.

DETAILED DESCRIPTION OF THE INVENTION

It has been discovered unexpectedly that certain derivatives of d4T possess increased activity against HIV while maintaining low levels of cytotoxicity. As such, these derivatives are particularly useful as active agents for antiviral compositions, and for methods of treating viral infections such as HIV infections.

COMPOUNDS OF THE INVENTION

Figure 5A:
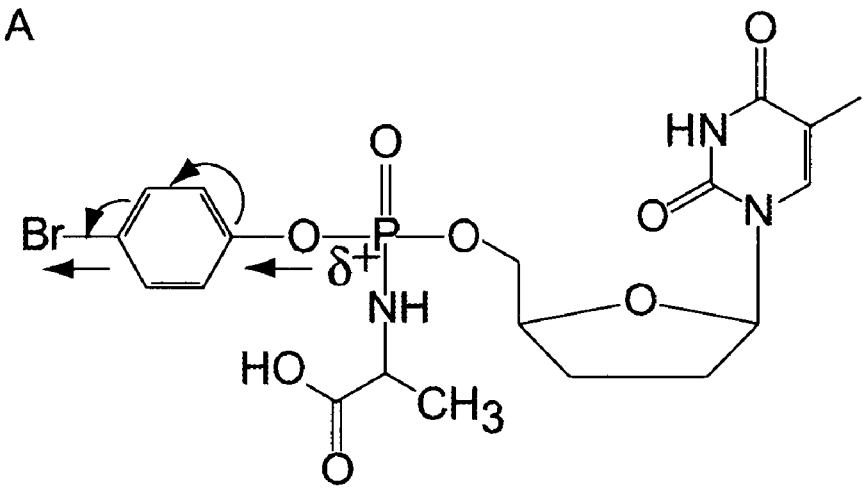
FIGS. 5A and 5B are schematic diagrams showing resonance effect (electron delocalization) of at the phenyl ring, whereby the para-substituent and ortho-substituent of phenyl ring are expected to have the same electronic effect.
Figure 5B:
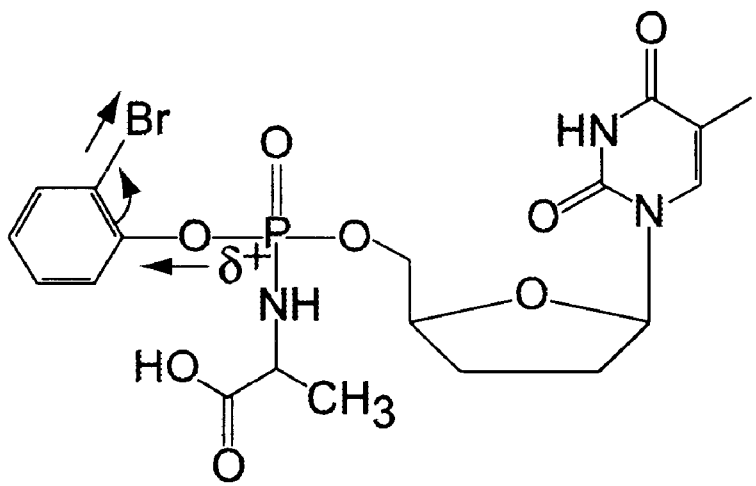

The compounds of the invention, as discussed more fully in the Examples below, are derivatives of d4T and AZT having potent antiviral activities. Compounds substituted with an electron-withdrawing group, such as an ortho or para substituted halogen or $NO_2$ as shown in FIGS. 5A and 5B, provide for more efficient hydrolysis to active inhibitory compounds. Preferred is halogen substitution, and most preferred is para-bromo substitution.

The d4T derivatives have aryl-phosphate substitution, with the aryl group having an electron-withdrawing substitution, such as an ortho or para-substitution with a halogen (Br, Cl, F, I) or with $NO_2$ substitution. One example is shown below, where $R_2$ is an amino acid residue that may be esterified or substituted, for example —NHCH($CH_3$)COOCH$_3$ or pharmaceutically acceptable salts or esters thereof.

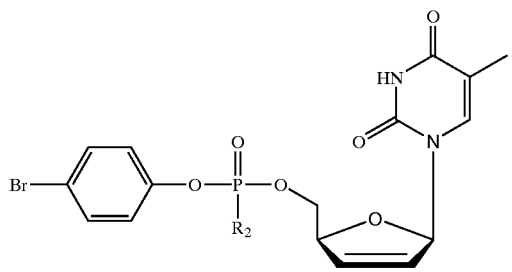

Synthesis of the d4T Derivatives

The d4T derivatives can be prepared as follows. d4T can be prepared from thymidine by the procedures discussed in Mansuri, et al., 1989 *J. Med. Chem.* 32, 461, the disclosure of which is incorporated herein by reference. Appropriately substituted aryl phosphorochloridate can be prepared by the procedures discussed in McGuigan, et al., *Antiviral Res.*, 1992, 17:311, the disclosure of which is incorporated herein by reference. The phosphorochloridate is added to a solution of d4T in anhydrous THF containing N-methylimidazole to form the desired product.

The d4T derivatives are administered to patients in the form of suitable compositions containing the d4T or AZT derivative as an active agent along with a pharmaceutically acceptable carrier, adjuvant or diluent. Sustained release dosage forms may be used if desired. The compositions are administered to a patient in need of the anti-viral activity in a suitable anti-viral amount, for example, sufficient to inhibit the HIV reverse transcriptase and/or inhibit replication of HIV in a host cells. The dose is administered according to a suitable dosage regimen.

EXAMPLES

The invention will be explained further with reference to the following examples, which should not be considered to limit the invention.

Example 1

Synthesis and Characterization of d4T Derivatives d4T 1 was prepared from thymidine following the procedure of Mansuri et.al., 1989 *J. Med.Chem.* 32, 461. Appropriately substituted phenyl methoxyalaninyl phosphorochloridates were also prepared according to the method reported by McGuigan et al 1992 *Antiviral Res.*, 17, 311. Compounds 2–4 were synthesized as outlined below in Scheme 1.

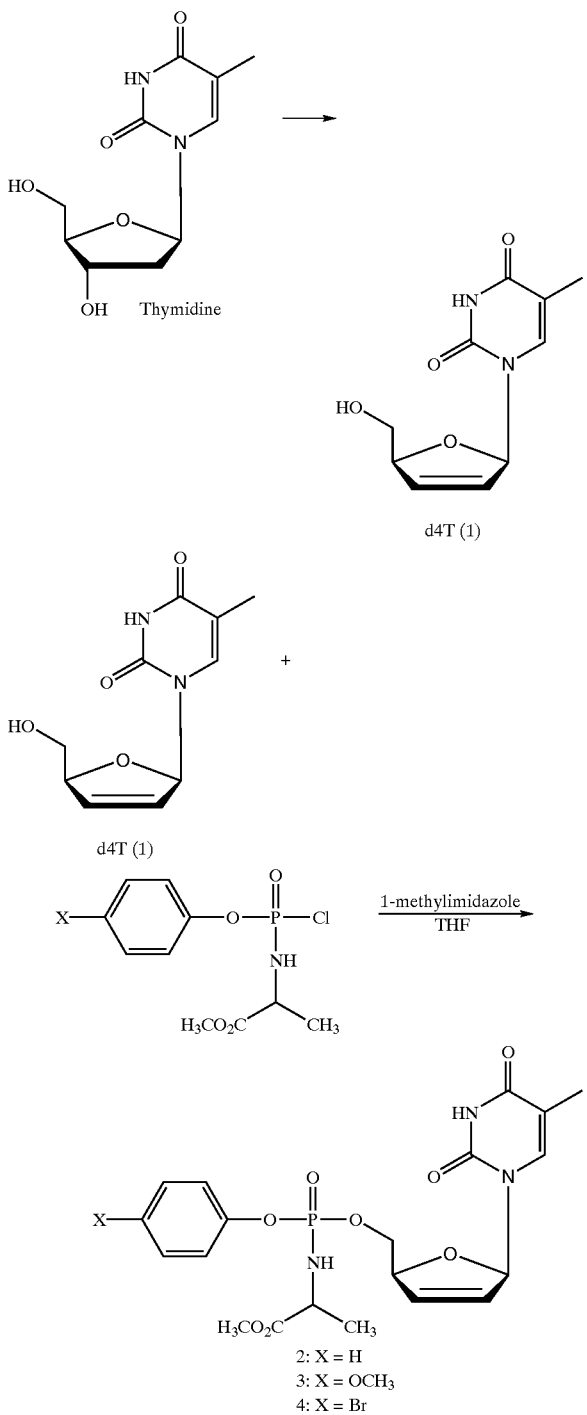

Scheme 1

Phenylmethoxyalaninyl phosphorochloridate was added to the solution of d4T and 1-methylimidazole in anhydrous THF and the mixture was stirred at room temperature for 5–6 hours. Work up of the reaction mixture furnished the required derivatives in good yields. Column chromatography was applied to obtain pure compounds.

Physical data of the synthesized compounds was determined by HPLC was conducted by using C18 4×250 mm LiChrospher column eluted with 70:30 water/acetonitrile at the flow rate of 1 ml/minute. The purity of the following compounds exceeded 96% by HPLC. $^{13}$C NMR peaks labeled by stars are split due to diastereomers.

Compound 2: yield: 81%; IR (Neat): 3222, 2985, 2954, 1743, 1693, 1593, 1491, 1456, 1213, 1153, 1039, 931, 769 cm$^{-1}$; $^1$H NMR (CDCl$_3$) δ 9.30 (br s, 1H), 7.30–7.10 (m, 6H), 6.85–6.82 (m, 1H), 6.36–6.26 (m, 1H), 5.91–5.85 (m, 1H), 5.00 (br m, 1H), 4.19–3.68 (m, 4H), 3.72, 371 (s, 3H), 1.83, 1.80 (d, 3H), 1.38–1.25 (m, 3H); $^{13}$C NMR(CDCl$_3$) δ 173.9, 163.7, 150.7, 149.7, 135.7*, 133.2*, 129.6*, 127.3*, 125.0*, 120.0, 111.1, 89.6*, 84.5*, 66.9*, 52.5*, 50.0*, 20.9 and 12.3; $^{31}$P NMR(CDCl$_3$) δ 2.66, 3.20; MALDI-TOF mass m/e 487.9 (M+Na); HPLC retention time: 5.54 & 5.85 minutes.

Compound 3: yield: 92%; IR (Neat): 3223, 3072, 2999, 2953, 2837, 1743, 1693, 1506, 1443, 1207, 1153, 1111, 1034, 937, 837 and 756 cm$^{31}$ $^1$; $^1$H NMR(CDCl$_3$) δ 9.40 (br s, 1H), 7.30–7.00 (m, 5H), 6.83–6.81 (m, 1H), 6.37–6.27 (m, 1H), 5.91–5.86 (m, 1H), 5.00 (br m, 1H), 4.40–4.30 (m, 2H), 4.20–4.10 (m, 2H), 3.95–3.93 (s, 3H), 3.82–3.80 (s, 3H), 1.85–1.81 (s, 3H), and 1.39–1.29 (m, 3H); $^{13}$C NMR (CDCl$_3$) δ 174.0, 163.9, 156.6, 150.8, 143.5, 135.8*, 133.3*, 127.4*, 121.2*, 114.5, 111.2, 89.7*, 84.5, 66.9*, 55.5, 52.5, 50.6*, 20.9, and 12.3; $^{31}$P NMR(CDCl$_3$) δ 3.82, 3.20; MALDI-TOF mass m/e 518.2 (M+Na); HPLC retention time: 5.83 & 6.26 minutes.

Compound 4: yield: 83%; IR (Neat): 3203, 3070, 2954, 2887, 2248, 1743, 1693, 1485, 1221, 1153, 1038, 912, 835, 733 cm$^{-1}$; $^1$H NMR(CDCl$_3$) δ 9.60–9.58 (br s, 1H), 7.45–7.42 (m, 2H), 7.30–7.09 (m, 4H), 6.37–6.27 (m, 1H), 5.93–5.88 (m, 1H), 5.04–5.01 (br m, 1H), 4.35–4.33 (m, 2H), 4.27–3.98 (m, 2H), 3.71–3.70 (s, 3H) , 1.85–1.81 (s, 3H), 1.37–1.31 (m, 3H); $^{13}$C NMR(CDCl$_3$) δ 173.7, 163.8, 150.8, 149.7*, 135.6*, 133.1*, 127.4*, 121.9*, 118.0, 111.2*, 89.7*, 84.4*, 67.8*, 52.5, 50.0*, 20.7, and 12.3; $^{31}$P NMR(CDCl$_3$) δ 3.41, 2.78; MALDI-TOF mass m/e 567.1 (M+Na); HPLC retention time: 12.04 & 12.72 minutes.

Example 3

Susceptibility of Compounds 2–4 to Hydrolysis

Figure 2A:
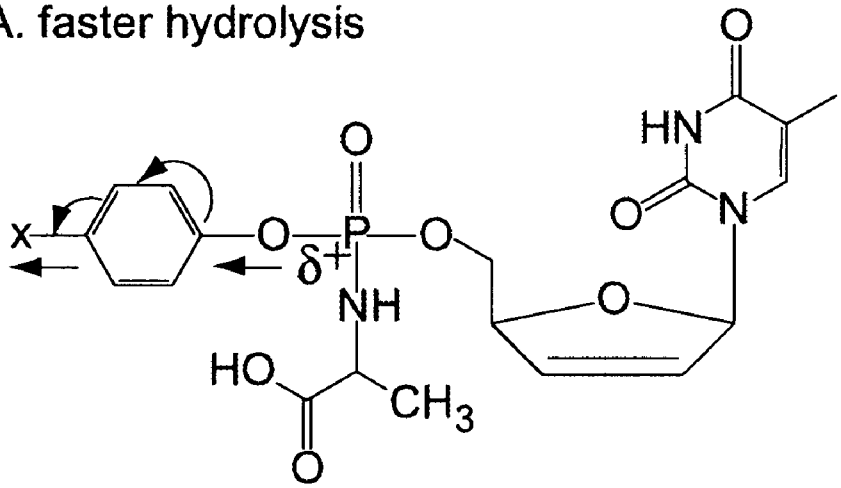
FIGS. 2A and 2B are diagrams showing the electron withdrawing hypothesis for the enhanced hydrolysis of a substituted phenyl ring.
Figure 2B:
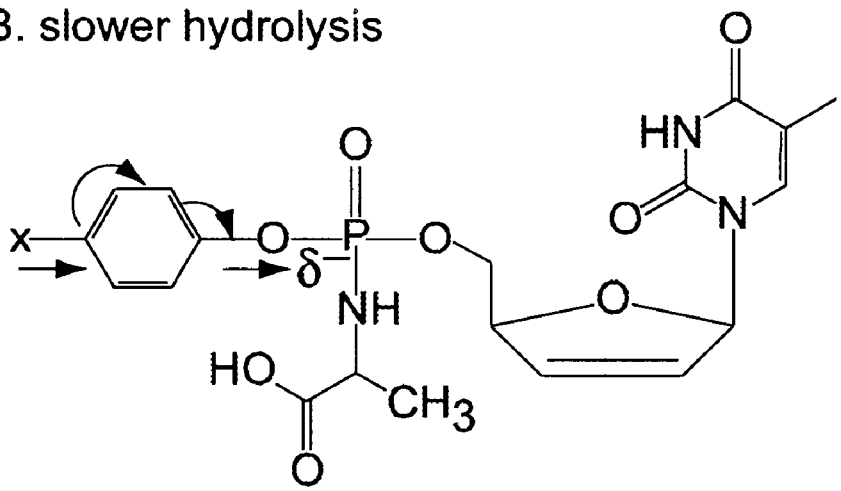

FIGS. 2A and 2B show a schematic representation of the electronic effects of the para substituent in the phenyl ring of metabolite precursor B (see FIG. 1). To assess the susceptibility of compounds to hydrolysis, Compounds 2–4 were dissolved in methanol and then treated with 0.002 N NaOH. The concentrations were kept constant and the generation of the hydrolysis product A-d4T-MP was monitored using HPLC. A Lichrospher column (C18) was used for the HPLC runs. The column was eluted under isocratic conditions using the solvent mixture 70:30 water/acetonitrile, and the elution profile is shown in FIG. 2C.

Hydrolysis of compounds was tested in a porcine liver esterase system. The data are shown in FIG. 2C. Compounds 2 and 4 (1 mM in Tris-HCl) were incubated with 100 U of porcine liver esterase (Sigma) in Tris-HCl buffer (pH 7.4) for 2 hours at 37° C. Reaction was stopped by adding acetone and chilling the reaction mixture. Following centrifugation at 15,000×g, 0.1 mL aliquots of the reaction mixture were examined for the presence of the active metabolite A-d4T-MP by using a quantitative analytical HPLC method capable of detecting 50 pmols of the metabolite. The 0.1 mL aliquot of the reaction product of compound 4 contained 1.4 nmols of A-d4T-MP, wheras no metabolite was detected in the reaction product of compound 2.

As shown in FIGS. 2A and 2B, the presence of an electron withdrawing substituent at the para position of the phenyl moiety is likely to increase the hydrolysis rates of the phenoxy group in the metabolite precursor B (FIG. 2A and 2B) generated by the carboxyesterase-dependent first step (FIGS. 1, A to B) of the metabolic pathway of phenyl phosphate derivatives of d4T. A single bromo substitution at the para position of the phenyl ring would not interfere with the recognition and hydrolysis of this compound by the carboxyesterase (Step A to B in FIG. 1). An electronic effect induced by the electron-withdrawing para-bromo substituent would result in enhanced hydrolysis of phenoxy group C yielding D and subsequently E, the precursors of the key metabolite A-d4T-MP. In order to test this hypothesis, we compared the unsubstituted compound 2, para-methoxy (OCH$_3$) substituted compound 3, and para-bromo substituted compound 4 (=d4T-5'-[p-bromo-phenylmethoxyalaninyl phosphate] or d4T-pBPMAP), for their rate of chemical hydrolysis after treatment with 0.002 N NaOH by measuring the generation of alaninyl-d4T-monophosphate (A-d4T-MP).

Figure 2C:
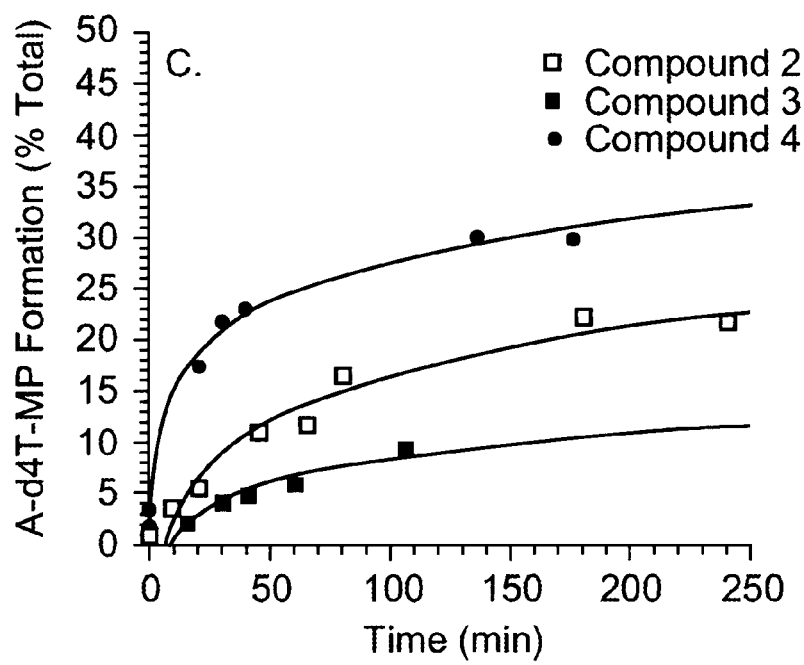
FIG. 2C is an elution profile showing production of A-d4T as a result of hydrolysis of each of the tested compounds: Compound 2, where X=H (open squares); Compound 3, where X=OCH$_3$ (filled squares); and Compound 4, where X=Br (filled circles).
Figure 2D:
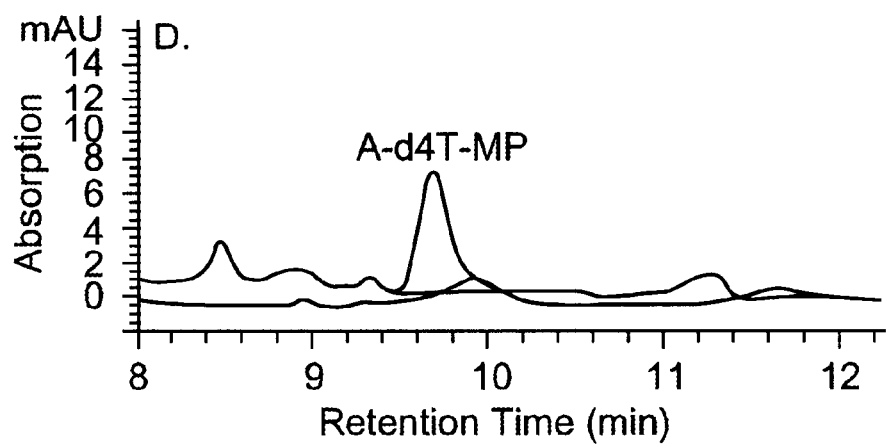
FIG. 2D is an elution profile showing the sensitivity of the tested compounds to enzymatic hydrolysis by porcine liver esterase.

As shown in FIG. 2C, compound 4 with a para-bromo substitent showed a much faster hydrolysis rate than the unsubstituted compound 2, whereas compound 3 with the electron donating substituent —OCH$_3$ at para position had a slower hydrolysis rate than either of those two compounds. Similarly, the lead compound 4 was more sensitive to enzymatic hydrolysis by porcine liver esterase than compound 2 (FIG. 2D).

Example 4

Intracellular Metabolism of Compounds 2–4 in TK-deficient CEM Cells

Figure 3:
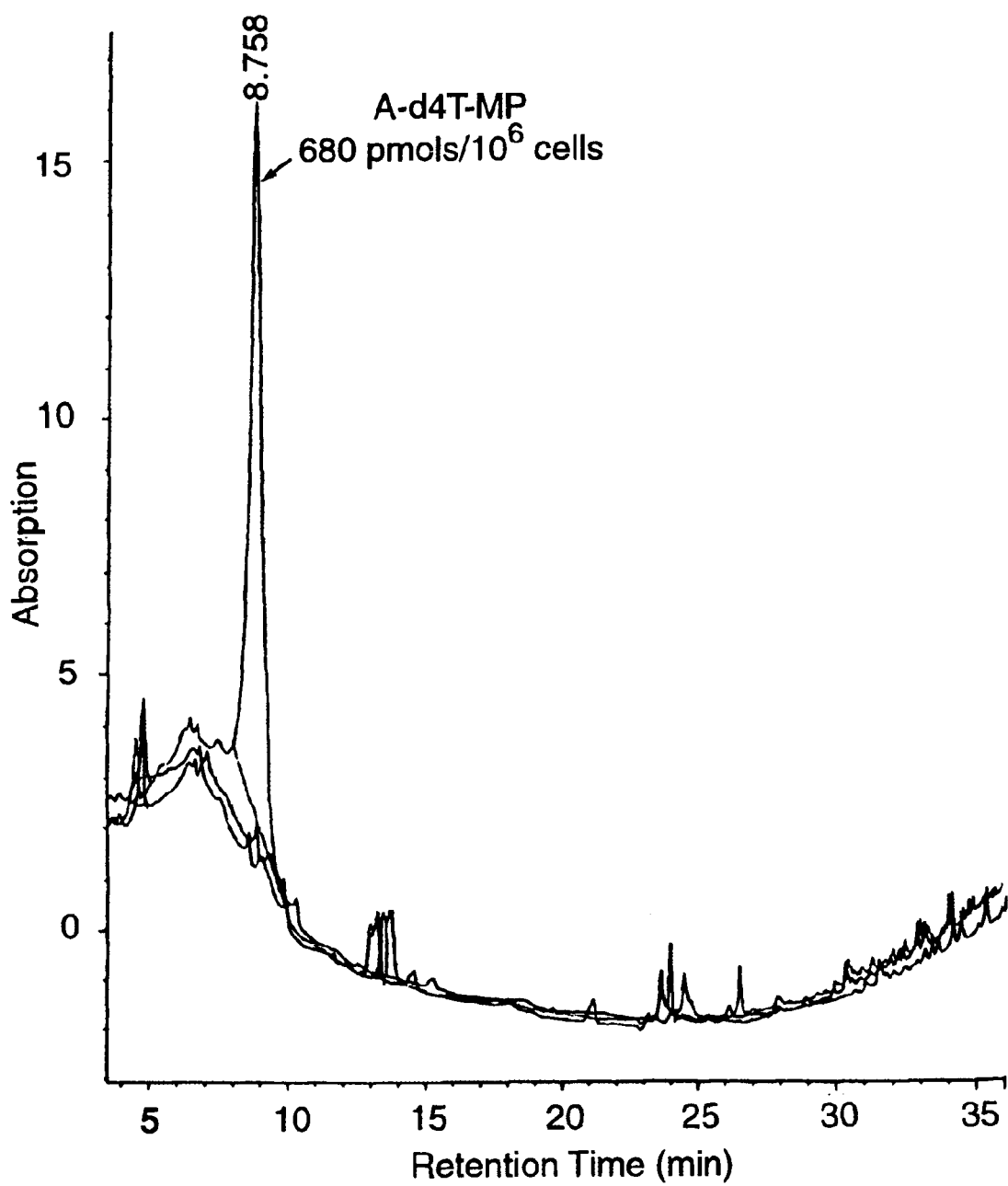
FIG. 3 is an elution profile showing the intracellular hydrolysis of compounds 2–4 in TK-deficient CEM cells. A metabolite peak with corresponding to 680 pmols of A-d4T-MP was detected only in aliquots from CEM cell lysates incubated with compound 4.
Figure 4B:
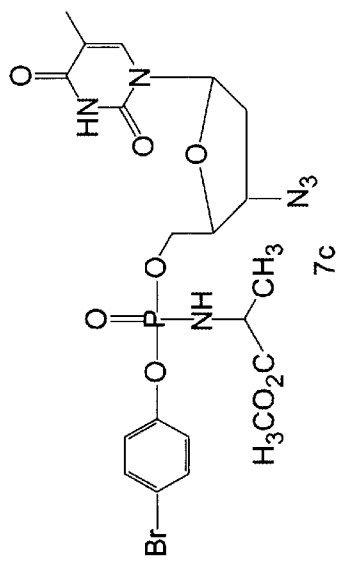
FIGS. 4A–4F show the chemical structures of compound 6c (FIG. 4A) and compound 7c (FIG. 4B); the anti-HIV activity against HTLV$_{IIIB}$ in PBMNC and TK-deficient CEM T-cells for compound 6c (FIG. 4C) and for compound 7c (FIG. 4D); and the antiviral activity against HIV-1 (HTLV$_{IIIB}$), HIV-2 and RTMDR-1 for compound 6c (FIG. 4E) and compound 7c (FIG. 4F). Antiviral activity was expressed as % inhibition of HIV replication as measured by RT activity in infected cells.
Figure 4D:
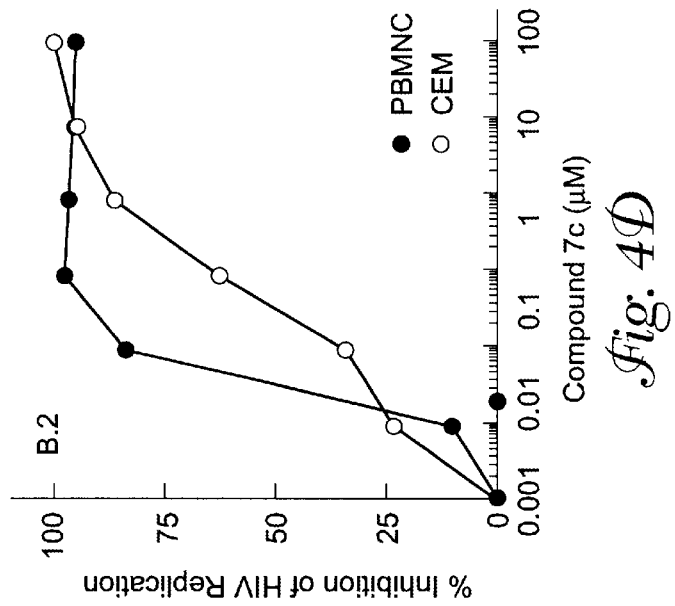
Figure 4A:
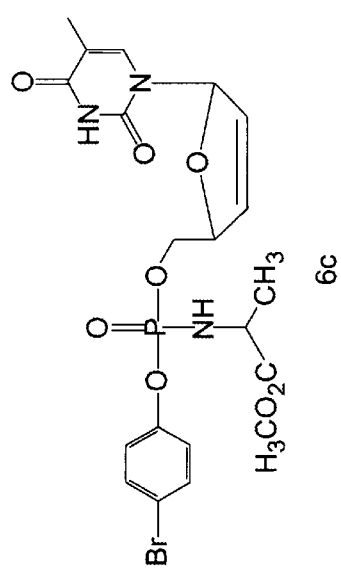
Figure 4C:
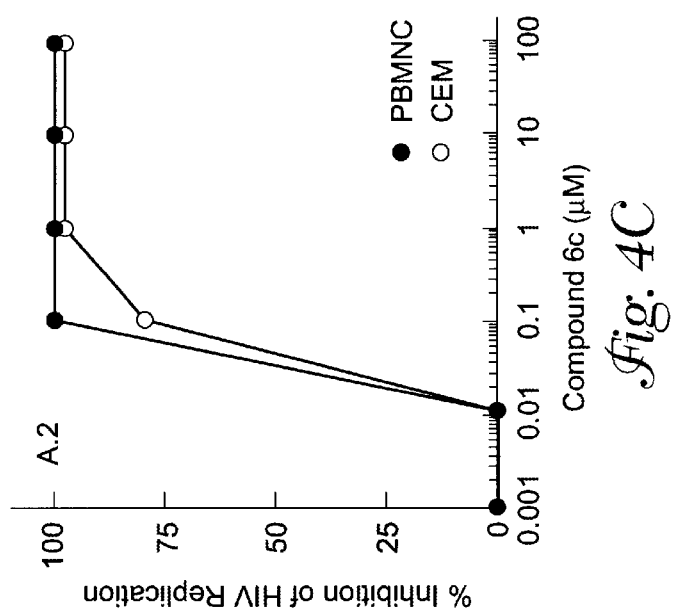
Figure 4F:
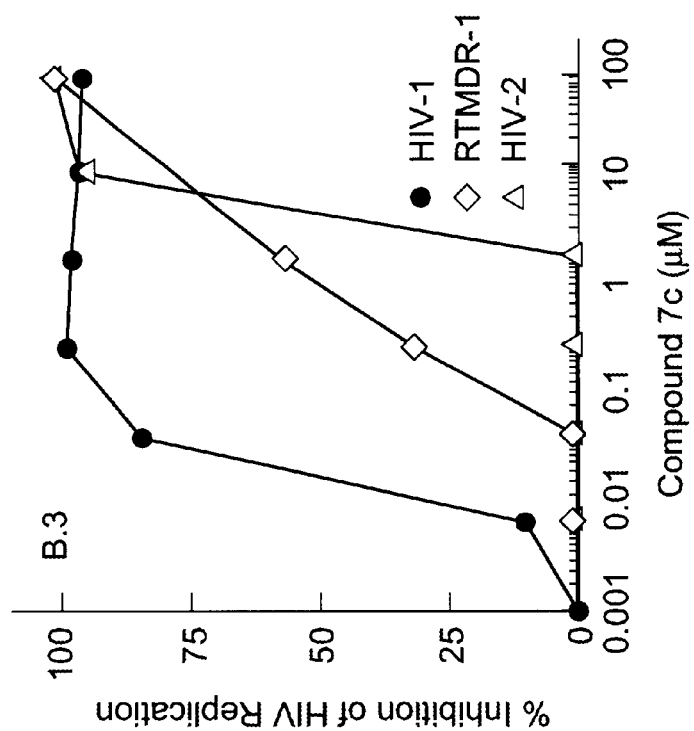
Figure 4E:
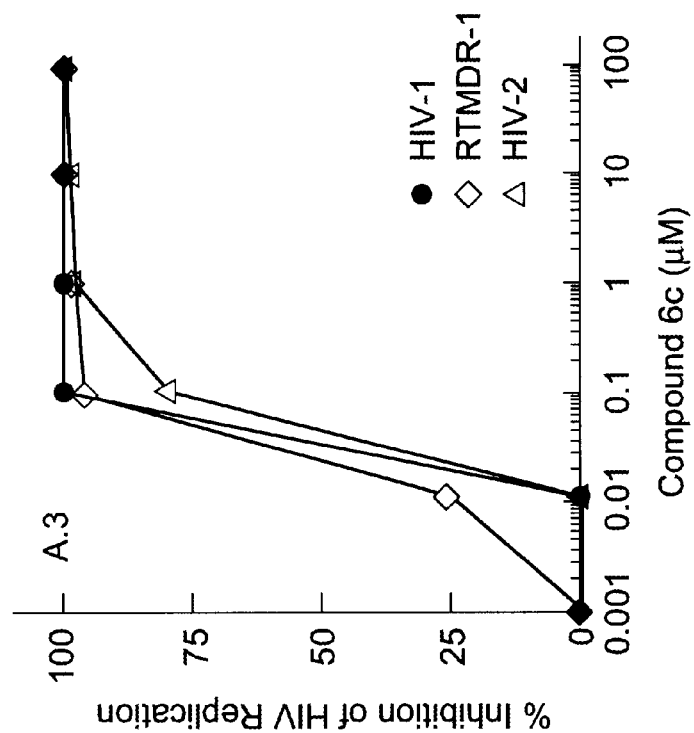

To analyze the intracellular metabolism of compounds 2–4 in TK-deficient cells, 1×10$^6$ CEM cells were incubated with compounds 2–4 (100 μM) for 3 hours and subsequently examined the formation of the partially hydrolyzed phosphate diester metabolite, alaninyl d4T monophosphate by HPLC. Notably, the amount of this metabolite in CEM cells treated with compound 4 was substantially greater than in CEM cells treated with compound 2 or 3 (680 pmol/10$^6$ cells vs <50 pmol/10$^6$ cells; FIG. 3).

CEM cells were cultured in a medium composed of RPMI, 10% fetal bovine serum, and 1% penicillin/streptomycin. Ten million cells at a density of 10$^6$ cells/mL were incubated with 100 μM of these compounds for 3 hours at 37° C. After incubation, cells were washed twice with ice-cold PBS, and extracted by addition of 0.5 mL of 60% methanol. Cell lysates were kept at −20° C. overnight, after which lysates were centrifuged at 15000×g for 10 minutes to remove the cell debris. One hundred μL aliquots of these lysates were injected directly to HPLC. The HPLC system consisted of a Hewlett Packard (HP) 1100 series equipped with a quarternary pump, an auto sampler, an electronic degasser, a diodearray detector, and a computer with a chemstation software program for data analysis. The samples were eluted on a 250×4.6 mm Sulpelco LC-DB C18 column. A solvent gradient was utilized to resolve the metabolite from the parent compound, which consisted of a mixture of methanol and 10 mM ammonium phosphate (pH 3.7). The gradient ran at a flow rate of 1 mL/minute from 5 to 35% methanol for the first 10 minutes, kept at 35% methanol for 5 minutes, and finished with a linear gradient from 35 to 100% methanol in the next 20 minutes. The detection wavelength was set at 270 nm. A metabolite peak with a retention time of 8.7 minutes corresponding to 680 pmols of A-d4T-MP was detected only in aliquots from CEM cell lysates incubated with compound 4.

Because of its enhanced susceptibility to hydrolysis, compound 4 was postulated to be a more potent anti-HIV agent than the other compounds. Compounds 2–4 as well as the parent compound d4T (1) were tested for their ability to inhibit HIV replication in peripheral blood mononuclear cells and TK-deficient CEM T-cells using previously described procedures (Zarling et.al., 1990 *Nature* 347:92; Erice et.al., 1993 *Antimicrob.Agents Chemother.* 37:835; Uckun et.al., 1998 *Antimicrob Agents Chemother.* 42:383). Percent inhibition of viral replication was calculated by comparing the p24 and RT activity values from the test substance-treated infected cells with those from untreated infected cells. In parallel, the cytotoxicity of the compounds was examined using a microculture tetrazolium assay (MTA) of cell proliferation, as described in the Zarling, Enrice, and Uckun articles Supra).

The similarity of the $IC_{50}$ values for inhibition of HIV-1 replication shown in Table 1, provide evidence that the d4T-aryl phosphate derivatives were not more potent than the parent compound d4T when tested in HIV-1-infected peripheral blood mononuclear cells. In accord with previous reports, the ability of d4T to inhibit HIV-1 replication was substantially reduced in TK-deficient CEM cells. Whereas the $IC_{50}$ value for inhibition of p24 production by d4T was 18 nM in peripheral blood mononuclear cells, it was 556 nM in TK-deficient CEM cells. Similarly, the $IC_{50}$ value for inhibition of RT activity increased from 40 nM to 2355 nM (Table 1). While all 3 aryl phosphate derivatives were more potent than d4T in TK-deficient CEM cells, compound 4 (d4T-5'-[p-bromo phenylmethoxyalaninyl phosphate]) having a para-bromo substituent in the aryl moiety, was 12.6-fold more potent in inhibiting p24 production ($IC_{50}$ values: 44 nM vs 556 nM) and 41.3-fold more potent in inhibiting the RT activity ($IC_{50}$ values: 57 nM vs 2355 nM) than d4T (Table 1).

TABLE 1

| | | PBMNC | | | CEM | | |
|---|---|---|---|---|---|---|---|
| Compound | X | $IC_{50}$ [p24] | $IC_{50}$ [RT] | $IC_{50}$ [MTA] | $IC_{50}$ [p24] | $IC_{50}$ [RT] | $IC_{50}$ [MTA] |
| 1 (= d4T) | | 0.018 | 0.040 | >10 | 0.556 | 2.355 | >10 |
| 2 | H | ND | ND | >10 | 0.145 | 0.133 | >10 |
| 3 | —OCH$_3$ | 0.033 | 0.033 | >10 | 0.106 | 0.320 | >10 |
| 4 | Br | 0.022 | 0.042 | >10 | 0.044 | 0.057 | >10 |

None of the tested compounds exhibited any detectable cytotoxicity to peripheral blood mononuclear cells or CEM cells at concentrations as high as 10,000 nM, as determined by MTA. Intriguingly, compound 3 with a para-methoxy substituent in the aryl moiety was 5.6-fold less effective than compound 4 in inhibiting the RT activity in HIV-infected TK-deficient CEM cells ($IC_{50}$ values: 320 nM vs 57 nM) although these two compounds showed similar activity in peripheral blood mononuclear cells ($IC_{50}$ values: 33 nM vs 42 nM). Thus, the identity of the para-substituent appears to affect the anti-HIV activity of the aryl phosphate derivatives of d4T in TK-deficient cells. To our knowledge, this is the first demonstration that the potency as well as the selectivity index of the d4T-aryl-phosphate derivatives can be substantially enhanced by introducing a single para-bromo substituent in the aryl moiety. This previously unknown structure-activity relationship determined by the aryl moiety of the phosphate derivatives of d4T provides a basis for the design of potentially more potent d4T analogues.

Example 5

Activity of Compound 4 and AZT in MDR Cells

The activity of compound 4 (d4T-5'-[p-bromophenyl methoxyalaninyl phosphate]) against HIV-MDR cells was compared with AZT-5'-[p-bromophenyl methoxyalaninyl phosphate] (P-AZT) and with AZT. The incubation and analysis methods used were as described above for Example 4.

As shown in Table 2, P-AZT and AZT have similar activities with the $IC_{50}$ values of 1.5 and 2.0 nM, respectively. The activity of Compound 4 (0.02 nM) is 100-fold more effective than AZT (2.0 nM).

TABLE 2

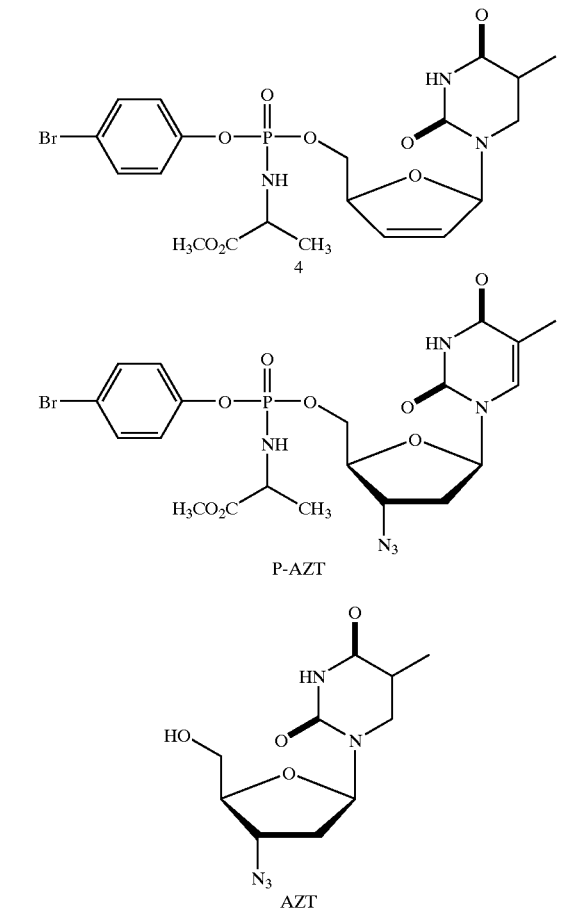

| Compound | HIV-2 $IC_{50}$ [RT] | HIV-MDR $IC_{50}$ [RT] |
|---|---|---|
| 4 | 0.4 | 0.02 |
| P-AZT | 3.9 | 1.5 |
| AZT | 2.4 | 2.0 |

Example 6

Synthesis of Arylphosphate Derivatives of 3dT

By way of further comparison, the effect on anti-HIV activity of various substitutions in the aryl group of arylphosphate derivatives of 3′-deoxytbymidine (3dT) was studied. As shown in Scheme 2, 3dt 5 was prepared from d4T 1 which was prepared from thymidine using the literature procedure (Mansuri et al., 1989 *J.Med.Chem.* 32:461–466). Hydrogenation of 1 was carried out in ethanol in the presence of $H_2$ and catalytic amount of 5% Pd/C to afford 3dT 5 in 85% yield. Appropriately substituted phenyl methoxyalaninyl phosphorochloridates were also prepared according to the method reported by McGuigan et.al., 1992 *Antiviral Res* 17:311–321, and compounds 6–11 were synthesized as outlined in Scheme 2.

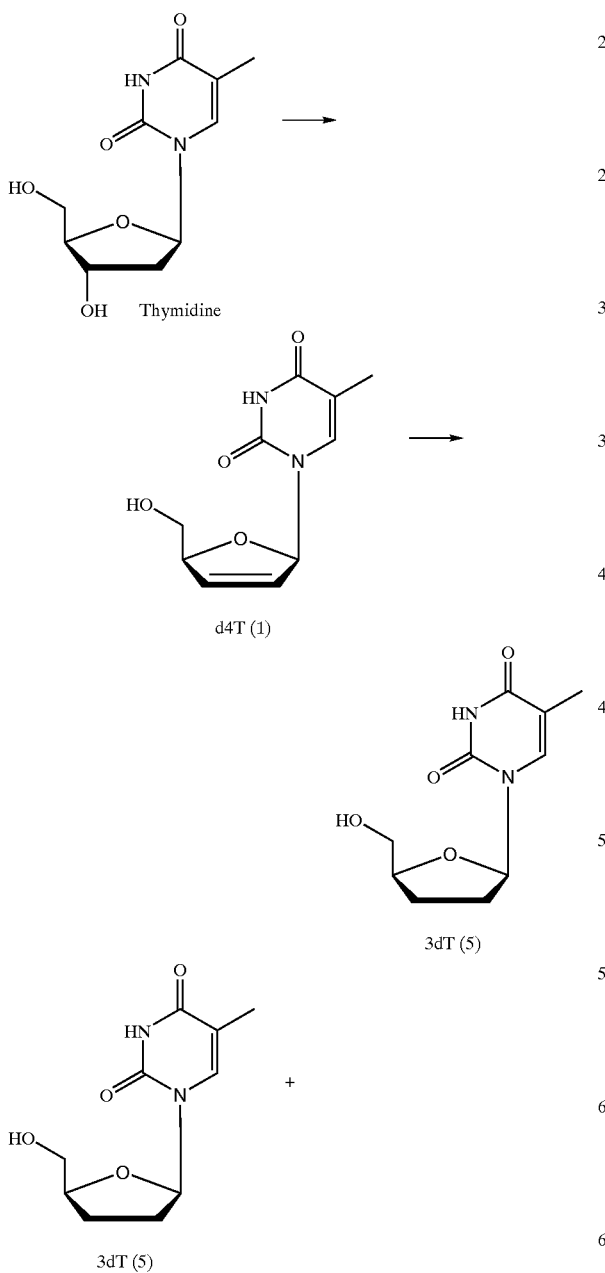

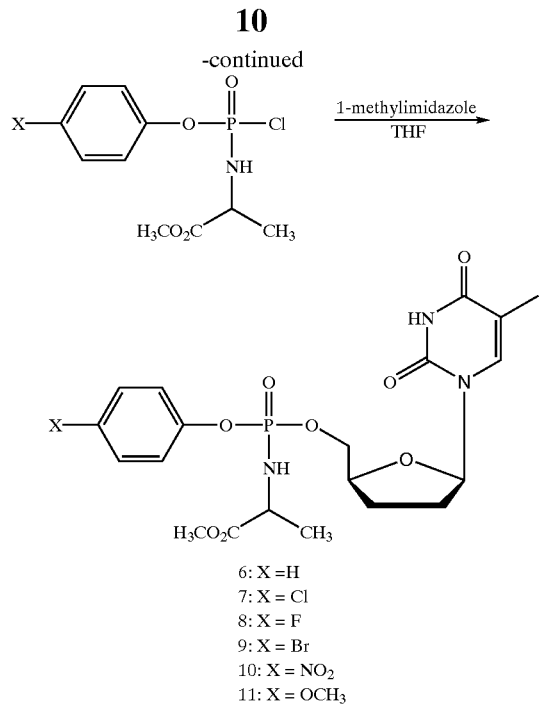

6: X = H
7: X = Cl
8: X = F
9: X = Br
10: X = $NO_2$
11: X = $OCH_3$

Scheme 2

The appropriately substituted phenyl methoxyalaninyl phosphorochloridate was added to a mixture of 3dT and 1-methylimidazole in anhydrous THF. The reaction mixture were stirred for 12 h at room temperature and then solvent was removed. The resulting gum was re-dissolved in chloroform and washed with 1M HCl, saturated sodium bicarbonate solution (except in the case of the $NO_2$ derivative) and then with water. The organic phase was dried by $MgSO_4$ and the solvent was removed in vacuo. The crude product was purified by silica gel flash column chromatography eluted with 5% methanol in chloroform to give pure compounds 6–11 in good yields.

Physical data of the synthesized compounds was determined. HPLC was conducted using C18 4×250 mm LiChrospher column eluted with 70:30 water/acetonitrile at the flow rate of 1 ml/minute. The purity of the following compounds exceed 96% by HPLC. $^{13}$C NMR peaks labeled by stars are split due to diastereomers.

Compound 5: yield: 85%; $^1$H NMR($CDCl_3$) δ 11.1 (br s, 1H), 7.82 (s, 1H), 5.97–5.94 (m, 1H), 5.10 (br s, 1H), 4.05–3.95 (m, 1H), 3.72–3.52 (m, 2H), 2.30–1.86 (m, 4H), 1.77 (s, 3H); $^{13}$C NMR($CDCl_3$) δ 163.9, 150.4, 136.4, 108.7, 84.8, 81.4, 62.2, 31.8, 25.1, and 12.5.

Compound 6: yield: 96%; IR (neat): 3211, 2955, 2821, 1689, 1491, 1265, 1211, 1153, 1043 and 933 $cm^{-1}$; $^1$H NMR($CDCl_3$) δ 10.1 (br s, 1H), 7.47 (s, 1H), 7.32–7.12 (m, 5H), 6.14–6.08 (m, 1H), 4.41–4.21 (m, 4H), 4.05–4.00 (m, 1H), 3.70, 3.69 (s, 3H), 2.37–2.32 (m, 1H), 2.05–1.89 (m, 7H), 1.38–1.35 (dd, 3H); $^{13}$C NMR($CDCl_3$) δ 173.6*, 163.8, 150.3, 150.1*, 135.2, 129.4*, 124.7, 119.8*, 110.5*, 85.7*, 78.3*, 67.2*, 52.3, 50.1*, 31.6*, 25.4*, 20.7*, and 12.4*; $^{31}$P NMR($CDCl_3$) δ 2.82 & 3.11; MS MALDI-TOF): 490.4 (M+Na); HPLC retention time=6.86, 7.35 minutes.

Compound 7: yield: 96%; IR (neat): 3217, 2954, 2821, 1743, 1689, 1489, 1265, 1217, 1153, 1092, 1012, 926 & 837 $cm^{-1}$; $^1$H NMR($CDCl_3$) δ 9.40 (br s, 1H), 7.43–7.41 (m, 1H), 7.30–7.14 (m, 4H), 6.13–6.07 (m, 1H), 4.39–4.00 (m, 5H), 3.71,3.70 (s, 3H), 2.38–2.36 (m, 1H), 2.09–1.89 (m, 5H), 1.39–1.36 (dd, 3H); $^{13}$C NMR($CDCl_3$) δ 173.6*, 163.7, 150.2, 148.8*, 135.3, 129.5–129.0, 121.5–121.3, 116.3, 110.6, 86.0*, 78.4*, 67.7*, 52.6*, 50.2*, 31.8*, 25.4*, 20.9* and 12.5; $^{31}$P NMR(CDCl$_3$) δ 2.87 & 3.09; MS (MALDI-TOF): 524.9 (M+Na); HPLC retention time=14.05, 14.89 minutes.

Compound 8: Viscous oil, yield: 96%; λ$_{max}$: 223 (ε3338) and 269 (ε4695) nm; IR (neat): 3211,:2955, 1743, 1693, 1500, 1569, 1265, 1197, 1153, 1045, 923 & 843 cm$^{-1}$; $^1$H NMR(CDCl$_3$) δ 9.40 (br s, 1H), 7.45–7.43 (d, 1H), 7.19–7.01 (m, 4H), 6.14–6.06 (m, 1H), 4.39–3.97 (m, 5H), 3.71, 3.70 (s, 3H), 2.38–1.89 (m, 7H), 1.39–1.35 (t, 3H); $^{13}$C NMR(CDCl$_3$) δ 173.6*, 163.7, 150.2, 150.1*, 135.3, 121.5*, 116.3*, 110.6*, 85.9*, 78.4*, 67.7*, 52.6, 50.2*, 31.8*, 25.6*, 20.9*, and 12.5; $^{31}$P NMR(CDCl$_3$) δ 3.13 & 3.37; MS (MALDI-TOF): 508.2 (M+Na); HPLC retention time=8.38, 8.80 minutes.

Compound 9: yield: 83%; IR (neat): 3211, 2954, 1743, 1689, 1485, 1265, 1217, 1153, 1010, 923 & 833 cm$^{-1}$; $^1$H NMR(CDCl$_3$) δ 9.82 (br s, 1H), 7.45–7.41 (m, 3H), 7.15–7.11 (m, 2H), 6.14–6.06 (m, 1H), 4.39–4.00 (m, 5H), 3.71, 3.70 (s, 3H), 2.38–1.89 (m, 7H), 1.39–1.35 (dd, 3H); $^{13}$C NMR(CDCl$_3$) δ 173.6*, 163.8, 150.3, 148.5*, 135.2, 132.6*, 121.8*, 117.7, 110.6*, 85.9*, 78.3*, 67.2*, 52.5, 50.2*, 31.6*, 25.6*, 20.8*, and 12.5; $^{31}$P NMR(CDCl$_3$) δ 2.83 & 3.05; MS (MALDI-TOF): 570.0 (M+2+Na); HPLC retention time=15.50, 16.57 minutes.

Compound 10: yield, 87%; IR (neat): 3203, 2955, 1743, 1684, 1593, 1522, 1348, 1265, 1153, 1101, 920 & 860 cm$^{-1}$; $^1$H NMR(CDCl$_3$) δ 9.51 (br s, 1H), 8.24–8.21 (m, 2H), 7.42–7.37 (m, 3H), 6.13–6.08 (m, 1H), 4.39–4.03 (m, 5H), 3.72, 3.71 (s, 3H), 2.38–1.89 (m, 7H), 1.41–1.38 (dd, 3H); $^{13}$C NMR(CDCl$_3$) δ 173.4*, 163.7, 155.2*, 150.2, 144.4, 135.3, 125.9–125.4, 120.6*, 115.4, 110.6*, 86.1*, 78.4*, 68.1*, 52.7, 50.2*, 31.7*, 25.8*, 20.9* and 12.5; $^{31}$P NMR (CDCl$_3$) δ 2.60 & 2.81; MS (MALDI-TOF): 535.0 (M+Na); HPLC retention time=8.12, 10.14 minutes.

Compound 11: yield, 100%; IR (neat): 3209, 2954, 1743, 1506, 1468, 1265, 1207, 1153, 1036, 937 & 835 cm$^{-1}$; $^1$H NMR(CDCl$_3$) δ 9.89 (br s, 1H), 7.49–7.47 (m, 1H), 7.16–7.11 (m, 2H), 6.84–6.80 (m, 2H), 6.15–6.09 (m, 1H), 4.39–4.02 (m, 5H), 3.77, 3.76 (s, 3H), 3.74, 3.73 (s, 3H), 2.38–1.89 (m, 7H), 1.38–1.33 (t, 3H); $^{13}$C NMR(CDCl$_3$) δ 173.7*, 163.9, 156.3, 150.3, 143.7*, 135.2, 120.7*, 114.3*, 110.5,85.7*, 78.4*, 67.3*, 55.4, 52.4, 50.1*, 31.8*, 25.4*, 20.8* and 12.4* ; $^{31}$P NMR(CDCl$_3$) δ 3.27 & 3.52; MS (MALDI-TOF): 521.3 (M+1+Na); HPLC retention time= 7.15, 7.66 minutes.

Example 7

Antiviral Activity of 3dT Compounds 6–11

Compounds 6–11 as well as the parent compound 3dT were tested in side-by-side comparison with d4T for their ability to inhibit HIV-1 replication in peripheral blood mononuclear cells and TK-deficient CEM T-cells using previously described procedures (Zarling et al., 1990; Erice et al., 1993; Uckun et al., 1998, Supra).

3dT as well as its derivatives were less active than d4T in peripheral blood mononuclear cells as well as TK-deficient CEM T-cells (Table 3). Notably, in peripheral blood mononucleare cells, the IC$_{50}$[RT] values for compounds 6–11 were higher than the IC$_{50}$[RT] value of 3dT (1.2–3.1 versus 0.7, Table 3), suggesting that these prodrugs are sufficiently stable and TK-independent steps in their metabolism, perhaps their enzymatic hydrolysis, may be rate-limiting for generation of active species. In contrast, aryl phospate derivatives of d4T were reported to be more potent than d4T suggesting that the TK-dependent generation of d4T monophospate is rate-limiting in its metabolic activation (McGuigan et al., 1996a). In accordance with the reported results in the literature regarding the biologic activity of aryl phospate derivatives of d4T and AZT (McGuigan et al., 1993, 1996a), the aryl phosphate derivatives of 3dT were more active than the parent compound 3dT in inhibiting HIV-1 replication in TK-deficient cells, albeit with still high micromolar IC$_{50}$[RT] values (Table 3).

Since compounds 6–11 were less active in TK-deficient CEM T-cells than they were in peripheral blood mononuclear cells (PBMNC), it was postulated that the conversion of 3dT monophosphate generated from these prodrugs into its active triphosphate occurs at a much slower rate in the absence of TK. By comparison, the aryl phospate derivatives of d4T showed similar activity in normal and TK-deficient cells (McGuigan et al., 1996 Bioorg.Med-.Chem.Lett. 6:1183–1186).

Anti-HIV Activity of aryl phosphate Derivatives of 3'-deoxythymidine (6–11) in Normal Peripheral Blood Mononuclear Cells (PBMNC) and TK-deficient CEM T-cells All data are in μM and represent concentrations required to inhibit viral replication, as measured by assays of RT activity, by 50% (IC$_{50}$ [RT])[9] or the 50% cytotoxic concentration, as measured by MTA(IC$_{50}$[MTA]) (Mansuri et.al., 1989 J. Med.Chem. 32:461).

TABLE 3

| Compound | X | PBMNC | | CEM | |
| --- | --- | --- | --- | --- | --- |
| | | IC$_{50}$ [RT] | IC$_{50}$ [MTA] | IC$_{50}$ [RT] | IC$_{50}$ [MTA] |
| 6 | H | 2.1 | >100 | 7.5 | >100 |
| 7 | Cl | 2.1 | >100 | 21.9 | >100 |
| 8 | F | 3.1 | >100 | 32.7 | >100 |
| 9 | Br | 1.2 | >100 | 22.8 | >100 |
| 10 | NO$_2$ | 2.0 | >100 | 22.6 | >100 |
| 11 | OMe | 1.3 | >100 | 19.7 | >100 |
| 3dT | — | 0.7 | >100 | 91.2 | >100 |
| d4T | — | 0.004 | >100 | 2.335 | >100 |

As shown in FIGS. 5A and 5B, the electronic effect of the para substitutions in the phenyl ring should affect the hydrolytic conversion of B to D in the metabolic pathway of aryl phospate derivatives of 3dT depicted in FIG. 1. The presence of an electron-withdrawing substituent at the para position of the phenyl moiety was expected to increase the hydrolysis rates of the substituted phenoxy groups in compounds 7–10 (FIG. 2A and 2B). However, these compounds were not more active than compound 6 with no para substitution or compound 11 with an electron donating para substituent, prompting the hypothesis that the carboxyesterase-dependent first hydrolysis step in their metabolism (A to B in FIG. 1) plays a critical and rate-limiting role for the generation of active 3dT metabolites. Thus, compounds 7–10 may serve as relatively poor substrates for the putative carboxyesterase responsible for their hydrolysis according to metabolic pathway proposed for aryl methoxyalaninyl phosphate derivatives of nucleoside analogs (McIntee et al., 1997 J.Med.Chem. 40:3323–3331).

In summary, the aryl phospate derivative of 3dT did not behave as what might have been expected from published work regarding the metabolism and activity of the prodrug forms of a very similar nucleoside analog, d4T. Surprisingly, the aryl phospate derivatives of 3dT did not elicit promising anti-HIV activity in HIV-1 infected normal peripheral blood mononuclear cells or TK-deficient CEM T-cell line.

Example 8

Anti-HIV Activity of Derivatives of d4T, AZT, and 3dT

As shown in Scheme 1, d4T 1 was prepared from thymidine using the literature procedure (Mansuri et.al., 1989, Supra). Hydrogenation of 1 in ethanol in the presence of $H_2$ and catalytic amount of 5% Pd/C afforded 3dT 3 in 85% yield (Scheme 1).

AZT 2 was prepared from thymidine using the literature methods (Chu et.al., U.S. Pat. No. 4,841,039). The ddN phosphorylation agents possessing different substituents in their phenoxy moieties 5a, 5b and 5c were prepared from the commercially available phenols in two-step procedures (Scheme 2) (McGuigan et.al., 1992, Supra),where Compounds 4a, 4b, 5a, 5b, 7a and 7b were previously reported. Compounds 4c and 5c are novel and their synthetic procedures as well as charaterization data are reported below.

The synthesis of phenyl methoxyalaninyl phosphate derivatives of d4T 1, AZT 2 or 3dT 3 was carried out by following the literature condition as shown in Scheme 3.(McGuigan et.al., 1992). The general synthetic procedures are as follows: The appropriately substituted phenyl methoxyalaninyl phosphorochloridate 5 was added to a mixture of the desired ddN (1, 2 or 3) and 1-methylimidazole in anhydrous THF. The reaction mixture were stirred for 12 hours at room temperature and then solvent was removed. The resulting gum was re-dissolved in chloroform and washed with 1M HCl, saturated sodium bicarbonate solution and then with water. The organic phase was dried by $MgSO_4$ and the solvent was removed in vacuo. The crude product was purified by silica gel flash column chromatography using a solvent mixture of methanol and chloroform for elution to give the desired pure compounds in good yields.

Scheme 1
Synthesis of d4T and 3dT

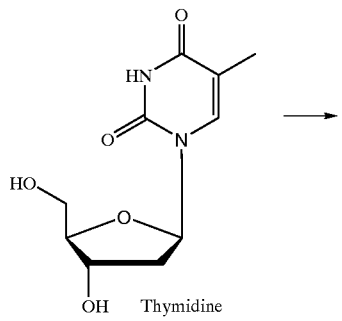
Thymidine

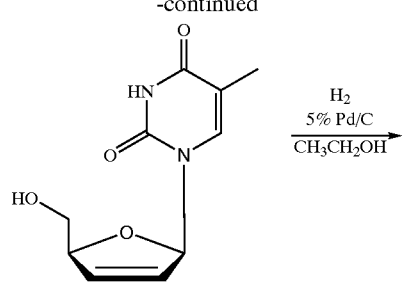
d4T (1)

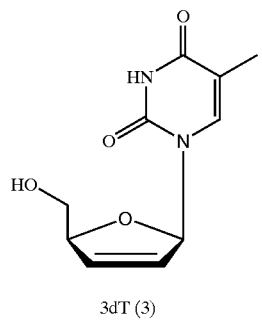
3dT (3)

Scheme 2
Synthesis of phenyl methoxyalaninyl phosphorochloridates

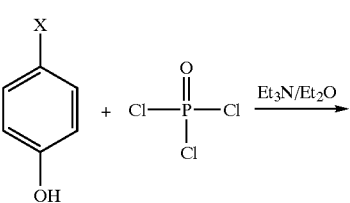

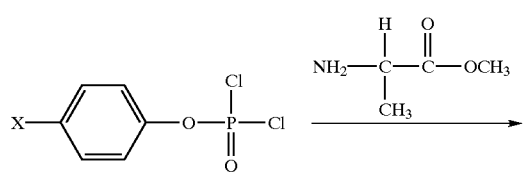

4a: X = H
4b: X = OCH$_3$
4c: X = Br

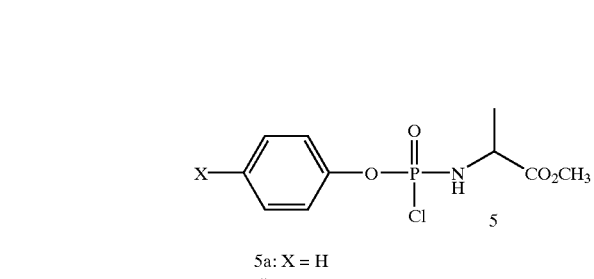

5a: X = H
5b: X = OCH$_3$
5c: X = Br

Scheme 3
Synthesis of phenyl methoxyalaninyl phosphate derivatives of ddN

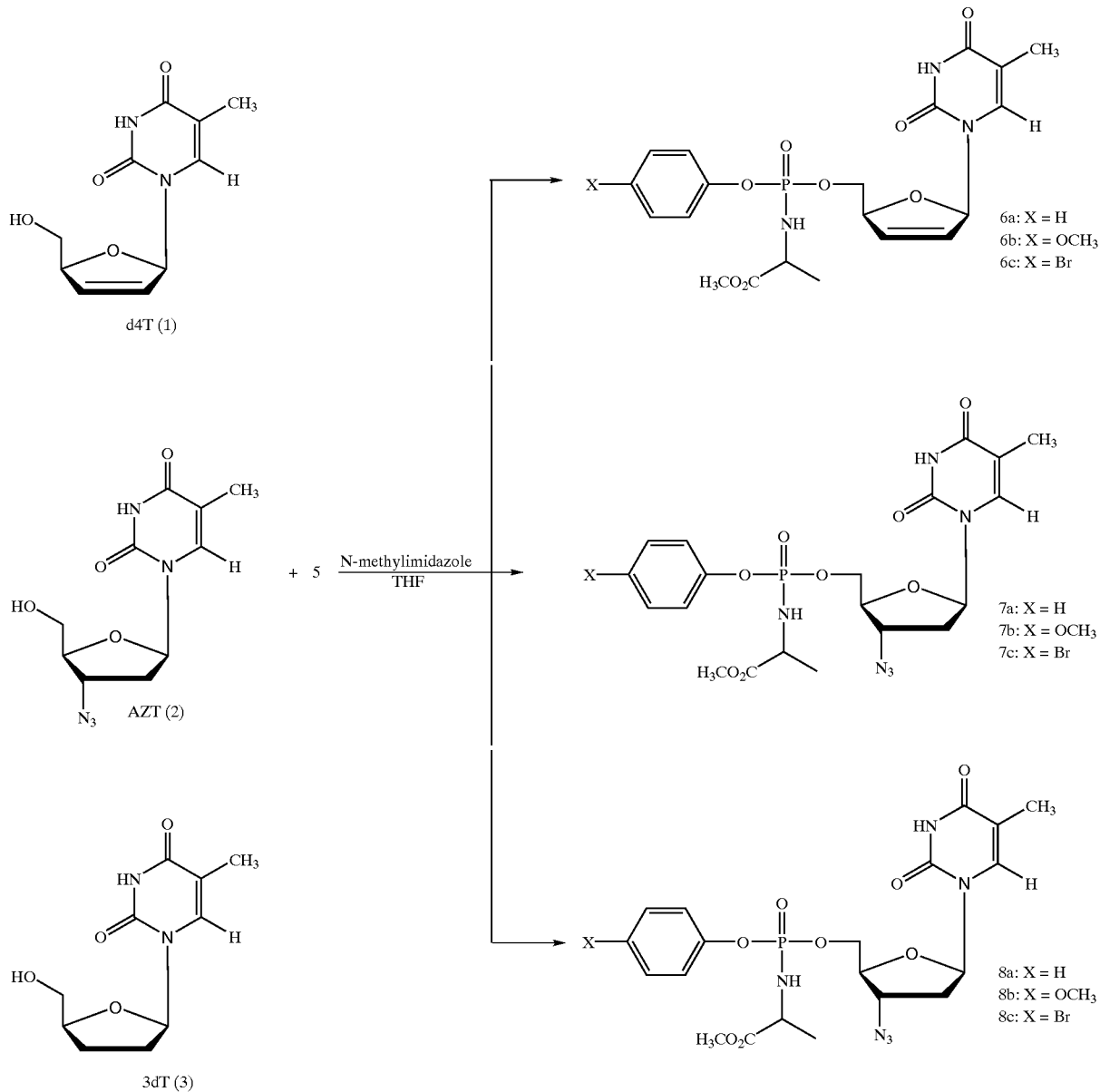

p-Bromophenyl phosphorodichloridate 4c

Following the procedure described by McGuigan et al., 1993, Supra, a solution of p-bromophenol (13.20 g; 76.30 mmol) and distilled triethylamine (10.65 mL) in anhydrous Et$_2$O (165 mL) was added dropwise into a vigorously stirred solution of phosphoryl chloride (8.5 mL; 91.2 mmol) in anhydrous Et$_2$O (83 mL) at 0° C. over a period of three hours under nitrogen atmosphere. Subsequently, the resultant mixture was gradually warmed up to room temperature, stirred efficiently overnight at room temperature and then heated to reflux for two hours. The reaction mixture was cooled to room temperature and filtered under aspirator pressure. The precipitate was washed with anhydrous Et$_2$O (2×50 mL). The combined Et$_2$O layers were evaporated to dryness on rotary evaporator to yield crude 4c as a pale yellow oil which was then subjected to vacuum distillation to give pure 4c (14.05 g; 63.5 % yield) as a colorless viscous oil (bp. 110–115° C./2 mm Hg). IR (Neat) 3095, 1481, 1303, 1187, 948, 829 cm$^{-1}$. $^1$H NMR (300 MHz, CDCl$_3$) δ 7.50 (2H, d, J=9.0 Hz), 7.15 (2H, d, J=9.0 Hz). GC/MS (m/e) 290 (M$^+$), 254 (M$^+$-Cl), 173 (M$^+$-POCl$_2$, $^{81}$Br), 171 (M$^+$-POCl$_2$, $^{79}$Br), 156 (M$^+$-PO$_2$Cl$_2$, $^{81}$Br), 154 (M$^+$-PO$_2$Cl$_2$, $^{79}$Br).

p-Bromophenyl methoxyalaninyl phosphorochloridate 5c

Following the procedure described by McGuigan et al., Supra, a solution of distilled triethylamine (8.80 mL; 63.14 mmol) in anhydrous CH$_2$Cl$_2$ (180 mL) was added dropwise via an addition funnel into a vigorously stirred solution of p-bromophenyl phosphorodichloridate 4c (8.69 g; 29.97 mmol) and L-alanine methyl ester hydrochloride (4.19 g; 30.02 mmol) in anhydrous CH$_2$Cl$_2$ (250 mL) at −70° C. over a period of three hours under nitrogen atmosphere. Subsequently, the resultant mixture was allowed to gradually warm up to room temperature and stirred overnight at room temperature. The solvent was removed on rotary evaporator. Anhydrous Et$_2$O (300 mL) was added to dissolve the residue and then filtered under aspirator pressure to remove the white solid. The white solid was rinsed with anhydrous Et$_2$O (2×60 mL). The Et$_2$O layers were combined and evaporated to dryness to afford a quantitative yield of 5c (10.7 g) as a pale pink-yellow viscous oil. This product was then used for the next step reaction without further purification. IR (Neat) 3212, 2989, 2952, 1747, 1483, 1270, 1209, 1147, 927, 831, 757 cm$^{-1}$. $^1$H NMR (300 MHz, CDCl$_3$) δ 8.70 (1H, br, Ala-NH), 7.48 (2H, d, J=9.0 Hz, aryl H), 7.16 (2H, d, J=9.0 Hz, aryl H), 3.79 & 3.77 (3H, s & s, —OCH$_3$), 1.51 & 1.40 (3H, d & d, Ala-CH$_3$). MS (CI, m/e) 357.9 (M$^+$, $^{81}$Br), 355.9 (M$^+$, $^{79}$Br), 322.0 (M$^+$-Cl, $^{81}$Br), 320.0 (M$^+$-Cl, $^{79}$Br), 297.9 (M$^+$-COOCH$_3$, $^{81}$Br), 295.9 ($^+$-COOCH$_3$, $^{79}$Br), 184.0 (M$^+$-BrC$_6$H$_4$O).

Characterization Data of phenyl methoxyalaninyl phosphate Derivatives of AZT 1, d4T 2 and 3dT 3

HPLC was conducted by using C18 4×250 mm LiChrospher column eluted with 70:30 water/acetonitrile at the flow rate of 1 ml/minute. The purity of the following compounds exceed 96% by HPLC. $^{13}$C NMR peaks labeled by asterisks were split due to diastereomers arising from the phosphorus stereocenters.

Compound 6a: yield: 81%; IR (Neat): 3222, 2985, 2954, 1743, 1693, 1593, 1491, 1456, 1213, 1153, 1039, 931. 769 cm$^{-1}$; $^1$H NMR (CDCl$_3$) δ 9.30 (br s, 1H), 7.30–7.10 (m, 6H), 6.85–6.82 (m, 1H), 6.36–6.26 (m, 1H), 5.91–5.85 (m, 1H), 5.00 (br m, 1H), 4.19–3.68 (m, 4H), 3.72, 3.71 (s, 3H), 1.83, 1.80 (d, 3H), 1.38–1.25 (m, 3H); $^{13}$C NMR(CDCl$_3$) 173.9, 163.7, 150.7, 149.7, 135.7*, 133.2*, 129.6*, 127.3*, 125.0*, 120.0, 111.1, 89.6*, 84.5*, 66.9*, 52.5*, 50.0*, 20.9 and 12.3; $^{31}$P NMR(CDCl$_3$) δ 2.66, 3.20; MALDI-TOF mass m/e 487.9 (M+Na); HPLC retention time: 5.54 & 5.85 minute.

Compound 6b: yield: 92%; IR (Neat): 3223, 3072, 2999, 2953, 2837, 1743, 1693, 1506,1443, 1207, 1153, 1111, 1034, 937, 837 and 756 cm$^{-1}$; $^1$H NMR(CDCl$_3$) δ 9.40 (br s, 1H), 7.30–7.00 (m, 5H), 6.83–6.81 (m, 1H), 6.37–6.27 (m, 1H ), 5.91–5.86 (m, 1H), 5.00 (br m, 1H), 4.40–4.30 (m, 2H), 4.20–4.10 (m, 2H), 3.95–3.93 (s, 3H), 3.82–3.80 (s, 3H), 1.85–1.81 (s, 3H) and 1.39–1.29 (m, 3H); $^{13}$C NMR(CDCl$_3$) δ 174.0, 163.9, 156.6, 150.8, 143.5, 135.8*, 133.3*, 127.4*, 121.2*, 114.5, 111.2, 89.7*, 84.5, 66.9*, 55.5, 52.5, 50.6*, 20.9, and 12.3; $^{31}$P NMR(CDCl$_3$) δ 3.82 3.20; MALDI-TOF mass m/e 518.2 (M+Na); HPLC retention time: 5.83 & 6.26 minute.

Compound 6c: yield: 83%; IR (Neat): 3203, 3070, 2954, 2887, 2248, 1743, 1693, 1485, 1221, 1153, 1038, 912, 835, 733 cm$^{-1}$; $^1$H NMR(CDCl$_3$) δ 9.60–9.58 (br s, 1H), 7.45–7.42 (m, 2H), 7.30–7.09 (m. 4H), 6.37–6.27 (m, 1H), 5.93–5.88 (m, 1H), 5.04–5.01 (br m, 1H), 4.35–4.33 (m, 2H), 4.27–3.98 (m, 2H), 3.71–3.70 (s, 3H) , 1.85–1.81 (s, 3H), 1.37–1.31 (m, 3H), 1.37–1.31 (m, 3H); $^{13}$C NMR (CDCl$_3$) δ 173.7, 163.8, 150.8, 149.7*, 135.6*, 133.1*, 127.4*, 121.9*, 118.0, 111.2*, 89.7*, 84.4*, 67.8*, 52.5, 50.0*, 20.7, and 12.3; $^{31}$P NMR(CDCl$_3$) δ 3.41, 2.78; MALDI-TOF m/e 567.1 (M+Na); HPLC retention time: 12.04 & 12.72 minute.

Compound 7c: yield: 95%; IR (Neat) 3205.7, 3066.3, 2954.5. 2109.8, 1745.3, 1691.3, 1484.9, 1270.9, 1153.2, 1010.5 and 926.1 cm$^{-1}$. $^1$H NMR (300 MHz, CDCl$_3$) δ 8.69 (1H, br, 3-NH), 7.45 (2H, d, J=9.0 Hz, aryl H), 7.34 & 7.32 (1H, s & s, vinyl H), 7.11 (2H, d, J=9.0 Hz, aryl H), 6.18 & 6.13 (1H, t & t, J=6.6 & 6.6 Hz. H at C-1'), 4.44–3.77 (6H, m, H at C-3', 4' & 5', Ala-NH and Ala-CH). 3.73 & 3.72 (3H, s & s, —COOCH$_3$), 2.51–2.20 (2H, m, H at C-2'), 2.18 (3H, s, —CH$_3$ at C-5), 1.39 & 1.36 (3H, d & d, Ala-CH$_3$). $^{13}$C NMR (75 MHz, CDCl$_3$) δ 173.6, 163.6, 150.1, 149.2, 149.1, 135.2, 132.4, 121.6, 117.8, 111.1, 85.0, 84.7, 81.9, 81.8, 65.5, 60.1, 59.9, 52.4, 50.0, 49.9, 36.9, 20.6, 20.5, 12.2. MS (CI, m/e) 589.1 (M$^+$, $^{81}$Br) and 587.1 (M$^+$, $^{79}$Br).

Compound 8a: yield: 96%; IR (Neat): 3211, 2955, 2821, 1689, 1491, 1265, 1211, 1153, 1043 and 933 cm$^{-1}$; $^1$H NMR(CDCl$_3$) δ 10.1 (br s, 1H), 7.47 (s, 1H), 7.32–7.12 (m, 5H), 6.14–6.08 (m, 1H), 4.41–4.21 (m, 4H), 4.05–4.00 (m, 1H), 3.70, 3.69 (s, 3H), 2.37–2.32 (m, 1H), 2.05–1.89 (m, 7H), 1.38–1.35 (dd, 3H); $^{13}$C NMR(CDCl$_3$) δ 173.6*, 163.8, 150.3, 150.1*, 135.2, 129.4*, 124.7, 119.8*, 110.5*, 85.7*, 78.3*, 67.2*, 52.3, 50.1*, 31.6*, 25.4*, 20.7*, and 12.4*; $^{31}$P NMR(CDCl$_3$) δ 2.82 & 3.11; MS (MALDI-TOF): 490.4 (M+Na); HPLC retention time=6.86, 7.35 minute.

Compound 8b: yield, 100%; IR (Neat): 3209, 2954, 1743, 1506, 1468, 1265, 1207, 1153, 1036, 937 & 835 cm$^{-1}$; $^1$H NMR(CDCl$_3$) δ 9.89 (br s, 1H), 7.49–7.47 (m, 1H), 7.16–7.11 (m, 2H), 6.84–6.80 (m, 2H), 6.15–6.09 (m, 1H), 4.39–4.02 (m, 5H), 3.77, 3.76 (s, 3H), 3.74, 3.73 (s, 3H), 2.38–1.89 (m, 7H), 1.38–1.33 (t, 3H); $^{13}$C NMR(CDCl$_3$) δ 173.7*, 163.9, 156.3, 150.3, 143.7*, 135.2, 120.7*, 114.3*, 110.5, 85.7*, 78.4*, 67.3*, 55.4, 52.4, 50.1*, 31.8*, 25.4*, 20.8* and 12.4*; $^{31}$P NMR(CDCl$_3$) δ 3.27 & 3.52; MS (MALDI-TOF): 521.3 (M+1+Na); HPLC retention time= 7.15, 7.66 minute.

Compound 8c: yield: 83%; IR (Neat): 3211, 2954, 1743, 1689, 1485, 1265, 1217, 1153, 1010, 923 & 833 cm$^{-1}$; $^1$H NMR(CDCl$_3$) δ 9.82 (br s, 1H), 7.45–7.41 (m, 3H), 7.15–7.11 (m, 2H), 6.14–6.06 (m, 1H), 4.39–4.00 (m, 5H), 3.71, 3.70 (s, 3H), 2.38–1.89 (m, 7H), 1.39–1.35 (dd, 3H); $^{13}$C NMR(CDCl$_3$) δ 173.6*, 163.8, 150.3, 148.5*, 135.2, 132.6*, 121.8*, 117.7, 110.6*, 85.9*, 78.3*, 67.2*, 52.5, 50.2*, 31.6*, 25.6*, 20.8*, and 12.5; $^{31}$P NMR(CDCl$_3$) δ 2.83 & 3.05; MS (MALDI-TOF): 570.0 (M+2+Na); HPLC retention time=15.50, 16.57 minute.

Cellular Assays of Anti-HIV Activity and Cytotoxicity

Anti-HIV activities were evaluated in AZT-sensitive HIV-1(strain: HTLV$_{IIIB}$)-, AZT- and NNI-resistant HIV-1(strain: RTMDR-1)—(kindly provided by Dr. Brendan Larder, NIH AIDS Research and Reference Reagent Program, DIV. AIDS, NIAID, NIH; cat. #2529), or HIV-2(Strain: CBL-20)-infected peripheral blood mononuclear cells (PBMNC) as well as HTLV$_{IIIB}$-infected TK-deficient CEM T-cells by determining the concentration of compound needed to inhibit viral replication by 50%, based on reverse transcriptase activity assays (IC$_{50}$ [RT]). Percent viral inhibition was calculated by comparing the RT activity values from the test substance-treated infected cells with RT values from untreated infected cells (i.e., virus controls). The 50% cytotoxic concentrations of the compounds (CC$_{50}$[MTA]) were measured by microculture tetrazolium assay (MTA), using 2,3-bis(2-methoxy-4-nitro-5-sulfophenyl)-5-[(phenylamino)-carbonyl]-2H-tetrazolium hydroxide (XTT) (Zarling et.al., 1990; Erice et.al., 1993, Uckun et.al., 1998, Supra).

Identification of d4T-5'-(para-bromophenyl methoxyalaninyl phosphate) and AZT-5'-(para-bromophenyl methoxyalaninyl phosphate) as Potent Anti-HIV Agents The d4T-phenyl phosphate derivatives were not more potent than the parent compound d4T when tested in HIV-1-infected PBMNC. The ability of d4T to inhibit HIV-1 replication was substantially reduced in TK-deficient CEM cells. Whereas the IC$_{50}$ value for inhibition of the RT activity by d4T was 40 nM in PBMNC, it was 2400 nM in TK-deficient CEM cells (Table 4 & FIGS. 4A–4F). While all three phenyl phosphate derivatives were more potent than d4T in TK-deficient CEM cells, compound 6c (d4T-5'-[p-bromo phenylmethoxyalaninyl phosphate]) with a para-bromo substituent in the phenyl moiety was 60-fold more potent in inhibiting the RT activity (IC$_{50}$ values: 60 nM vs 2400 nM) than d4T (Table 4).

None of the compounds exhibited any detectable cytotoxicity to PBMNC or CEM cells at concentrations as high as 10,000 nM, as determined by MTA. Intriguingly, compound 6b with a para-methoxy substituent in the phenyl moiety was 5-fold less effective than compound 6c in inhibiting the RT activity in HIV-infected TK-deficient CEM cells (IC$_{50}$ values: 300 nM vs 60 nM) although these two compounds showed similar activity in peripheral blood mononuclear cells (IC$_{50}$ values: 30 nM vs 40 nM) (Table 4).

Compounds 7a, 7b, 7c and their parent compound AZT 2 were tested for their ability to inhibit HIV replication in PBMNC and TK-deficient CEM T-cells (Table 4). Percent inhibition of viral replication was calculated by comparing the RT activity values from the test substance-treated infected cells with those from untreated infected cells. In parallel, the cytotoxicity of the compounds was examined using a microculture tetrazolium assay (MTA) of cell proliferation. The ability of AZT 2 to inhibit HIV-1 replication was substantially reduced in TK-deficient CEM cells. Whereas the IC$_{50}$ value for inhibition of RT activity by AZT was 3 nM in PBMNC, it was 200 nM in TK-deficient CEM cells. Unlike the corresponding d4T derivatives, the unsubstituted and para substituted phenyl phosphate derivatives of AZT were not more potent than the parent compound AZT when tested in HIV-1 infected TK-deficient CEM T-cells. However, the para-bromo substituted phenyl phosphate derivative of AZT, AZT-5'-(para-bromophenyl methoxyalaninyl phosphate) 7c, was 5 times more effective than AZT in inhibiting HIV replication of TK-deficient CEM cells (IC$_{50}$[RT] values: 0.04 µM vs 0.2 µM). None of the compounds exhibited any detectable cytotoxicity to PBMNC or CEM cells at concentrations as high as 10,000 nM, as determined by MTA.

Compounds 8a–c and their parent compound 3dT 3 were tested in side-by-side comparison with d4T 1 for their ability to inhibit HIV-1 replication in PBMNC and TK-deficient CEM T-cells. 3dT as well as its derivatives were less active than d4T in peripheral blood mononuclear cells as well as TK-deficient CEM T-cells (Table 4). Notably, in peripheral blood mononuclear cells, the IC$_{50}$[RT] values for compounds 8a–c were higher than the IC$_{50}$[RT] value of 3dT (1.2–3.1 versus 0.7, Table 4), suggesting that these prodrugs are sufficiently stable and TK-independent steps in their metabolism, perhaps their enzymatic hydrolysis, may be rate-limiting for generation of active species. In accordance with the reported results in the literature regarding the biologic activity of phenyl phospate derivatives of d4T and AZT the phenyl phosphate derivatives of 3dT were more active than the parent compound 3dT in inhibiting HIV-1 replication in TK-deficient cells, albeit with still high micromolar IC$_{50}$[RT] values (Table 4 & FIGS. 4A–4F). Since compounds 8a–c were less active in TK-deficient CEM T-cells than they were in PBMNC, we postulate that the conversion of 3dT monophosphate generated from these prodrugs into its active triphosphate occurs at a much slower rate in the absence of TK.

TABLE 4

Anti-HIV Activity of phenyl methoxyalaninyl phosphate derivatives of d4T, AZT and 3dT in normal peripheral blood mononuclear cells (PBMNC) and TK-deficient CEM T-cells.

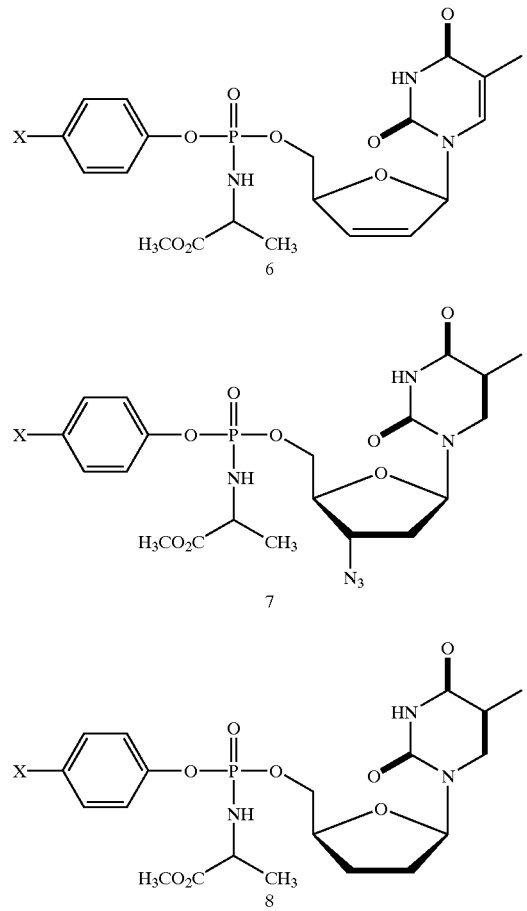

| Compound | X | PBMNC IC$_{50}$ [RT] | PBMNC IC$_{50}$ [MTA] | CEM IC$_{50}$ [RT] | CEM IC$_{50}$ [MTA] |
|---|---|---|---|---|---|
| 6a | H | N.D. | N.D. | 0.1 | >10 |
| 6b | OCH$_3$ | 0.03 | >10 | 0.3 | >10 |
| 6c | Br | 0.04 | >10 | 0.06 | >10 |
| 7a | H | N.D. | N.D. | 1.7 | >10 |
| 7b | OMe | 0.1 | >10 | 4.1 | >10 |
| 7c | Br | 0.004 | >10 | 0.04 | >10 |
| 8a | H | 2.1 | >10 | 7.5 | >10 |
| 8b | OMe | 1.3 | >10 | 19.7 | >10 |
| 8c | Br | 1.2 | >10 | 22.3 | >10 |
| 1 (d4T) | — | 0.04 | >10 | 2.4 | >10 |
| 2 (AZT) | — | 0.003 | >10 | 0.2 | >10 |
| 3 (3dT) | — | 0.7 | >10 | 91.2 | >10 |

Activity of the Lead Compounds d4T-5'-(para-bromophenyl methoxyalaninyl phosphate) and AZT-5'-(para-bromophenyl methoxyalaninyl phosphate) against HIV-2 and RTMDR-1

The lead compounds 6c and 7c were tested in side-by-side comparison with AZT 2 for their ability to inhibit HIV replication in RTMDR-1, an AZT- and NNI-resistant strain of HIV-1, and HIV-2 in PBMNC (Table 5). The novel d4T derivative 6c, d4T-5'-(para-bromophenyl methoxyalaninyl phosphate), had potent antiviral activity against RTMDR-1 and moderate activity against HIV-2. However, the corresponding para-bromo substituted phenyl methoxyalaninyl phosphate derivative of AZT 7c and the parent AZT 2 were not effective against the AZT resistant RTMDR-1 or against HIV-2.

TABLE 5

Anti-HIV Activity of lead compounds 6c and 7c in HIV-2 and RTMDR-1 cells.

[Structure of compound 6c: p-bromophenyl methoxyalaninyl phosphate derivative of d4T]

6c

[Structure of compound 7c: p-bromophenyl methoxyalaninyl phosphate derivative of AZT]

7c

[Structure of compound 2 (AZT)]

2 (AZT)

| Compound | HIV-2 IC$_{50}$ [RT] | RTMDR-1 IC$_{50}$ [RT] |
|---|---|---|
| 6c | 0.4 | 0.02 |
| 7c | 3.9 | 1.5 |
| 2 (AZT) | 2.4 | 2.0 |

All data are in $\mu$M and represent concentrations required to inhibit viral replication, as measured by assays of RT activity, by 50% (IC$_{50}$[RT]).

Compounds 6a, 6b and 6c are all more potent than the parent d4T 1 in TK-deficient CEM cells, while these d4T-phenyl phosphate derivatives (6a, 6b and 6c) are not more potent than the parent d4T 1 in HIV-1 infected PBMNC (Table 4). Comparing all the phenyl methoxyalaninyl phosphate derivatized d4T, d4T-5'-[p-bromo phenylmethoxy-alaninyl phosphate] 6c is the most potent anti-HIV agent in TK-deficient CEM cells. This observation could be attributed to the para-bromo substituent in the phenyl moiety of 6c which enhances the ability of its phosphorus to undergo hydrolysis due to the electron withdrawing property of the bromo substituent (FIG. 2) and results in generation of substantially higher quantities of the key metabolite d4T monophosphate in the TK-deficient CEM T-cells (McIntee et.al., 1997, *J.Med. Chem.* 40:3233–3331).

The potency of phenyl, methoxyphenyl and bromophenyl phosphate derivatives of AZT in TK-deficient CEM cells also followed the same trend as that of d4T derivatives, namely 7c (bromophenyl)>7a (phenyl)>7b (methoxyphenyl). However, among the three phenyl methoxyalaninyl phosphate derivatives of AZT (7a, 7b and 7c), only 7c showed higher potency than AZT in TK-deficient CEM cells (IC$_{50}$ values: 40 nM vs 200 nM). For phenyl methoxyalaninyl phosphate derivatives of 3dT (Table 4), the presence of an electron-withdrawing substituent at the para position of the phenyl moiety was expected to increase the hydrolysis rates of the substituted phenoxy group in compound 8c (e.g. B to C in FIG. 2). However, 8c was not more active than compound 8a with no para substitution or compound 8b with an electron donating para substituent, prompting the hypothesis that the carboxyesterase-dependent first hydrolysis step in their metabolism (e.g. A to B in FIG. 2) plays a critical and rate-limiting role for the generation of active 3dT metabolites. We postulate that compounds 8a, 8b and 8c may serve as relatively poor substrates for the putative carboxyesterase responsible for their hydrolysis according to metabolic pathway proposed for phenyl methoxyalaninyl phosphate derivatives of nucleoside analogs (FIG. 2). The aryl phospate derivatives of 3dT did not behave as what might have been expected from the published work regarding the metabolism and activity of the prodrug forms of a very similar nucleoside analog, d4T. To much of our surprise, the aryl phospate derivatives of 3dT did not elicit promising anti-HIV activity in HIV-1 infected normal peripheral blood mononuclear cells or TK-deficient CEM T-cell line.

In summary, d4T-5'-[p-bromo-phenylmethoxyalaninyl phosphate] 6c and AZT-5'-[p-bromo-phenylmethoxyalaninyl phosphate] 7c were identified as active anti-HIV agents which potently inhibit HIV replication in TK-deficient CEM T-cells without any detectable cytotoxicity. Furthermore, the novel d4T derivative 6c had potent antiviral activity against RTMDR-1, an AZT- and NNI-resistant strain of HIV-1, and moderate activity against HIV-2. In contrast to these d4T and AZT derivatives, the corresponding 3dT derivative, 3dT-5'-(para-bromophenyl methoxyalaninyl phosphate), showed no significant anti-HIV activity in PBMNC or TK-deficient CEM T-cells. To our knowledge, this is the first comprehensive report of a previously unappreciated structure activity relationship determining the potency of phenyl phosphate derivatives of d4T and AZT. Further development of the lead compounds 6c and 7c may provide the basis for the design of effective HIV treatment strategies capable of inhibiting HIV replication in TK-deficient cells.

While a detailed description of the present invention has been provided above, the invention is not limited thereto. The invention described herein may be modified to include alternative embodiments, as will be apparent to those skilled in the art. All such alternatives should be considered within the spirit and scope of the invention, as claimed below.

We claim:
1. A compound of the formula:

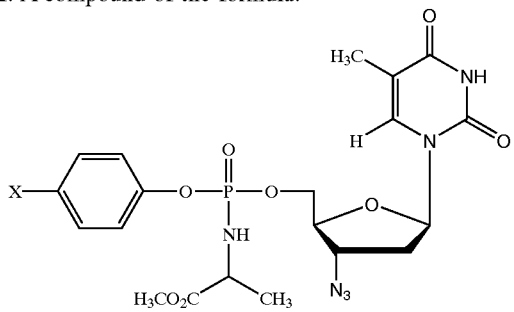

wherein

X is selected from Br and Cl;
or a pharmaceutically acceptable salt or ester thereof.

2. A compound of the formula:

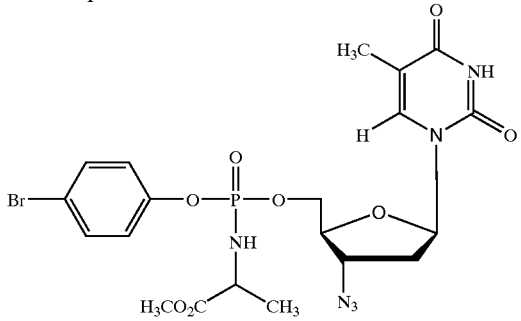

or a pharmaceutically acceptable salt or ester thereof.

3. A compound of the formula:

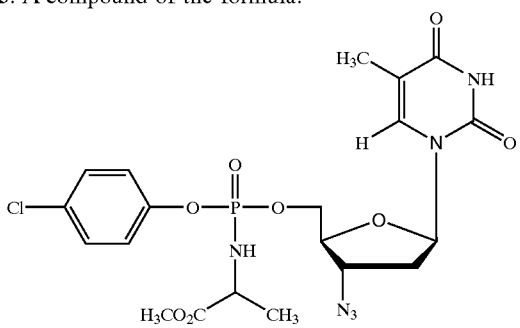

or a pharmaceutically acceptable salt or ester thereof.

4. A method for inhibiting virus replication in a cell infected with a virus, the method comprising administering to the infected cell a virus replication inhibiting amount of a compound of the formula:

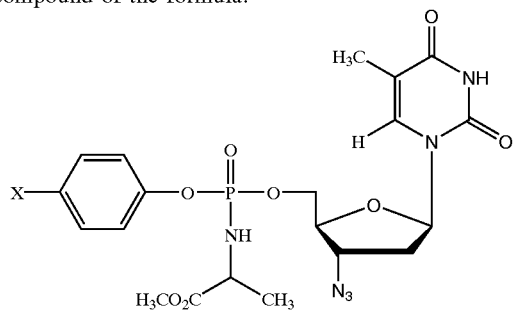

wherein

X is selected from Br and Cl;
or a pharmaceutically acceptable salt or ester thereof.

5. The method of claim 4, wherein X is Br.
6. The method of claim 4, wherein X is Cl.
7. The method of claim 4, wherein the virus comprises HIV.

8. A method of inhibiting virus reverse transcriptase in a cell infected with a virus, the method comprising administering to the infected cell a reverse transcriptase inhibiting amount of a compound of the formula:

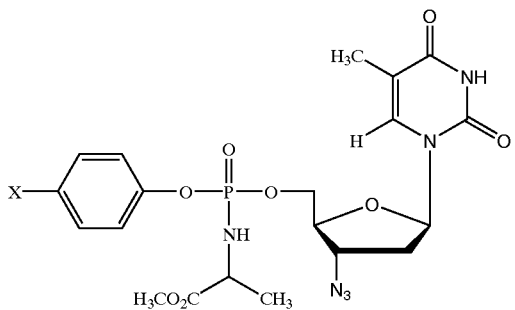

wherein

X is selected from Br and Cl;
or a pharmaceutically acceptable salt or ester thereof.

9. The method of claim 8, wherein X is Br.
10. The method of claim 8, wherein X is Cl.
11. The method of claim 8, wherein the virus comprises HIV.

12. A composition useful for inhibiting virus replication in a cell infected with a virus, the composition comprising an amount effective for inhibiting virus replication in the cell of a compound of the formula:

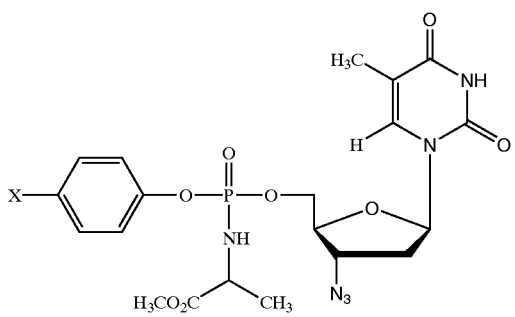

wherein

X is selected from Br and Cl;
or a pharmaceutically acceptable salt or ester thereof; and
a pharmaceutically acceptable carrier, adjuvant or diluent.

13. The composition of claim 12, wherein X is Br.
14. The composition of claim 12, wherein X is Cl.
15. The composition of claim 12, wherein the virus comprises HIV.

16. A composition useful for inhibiting virus reverse transcriptase in a cell infected with a virus, the composition comprising an amount effective for inhibiting virus reverse transcriptase in the infected cell of a compound of the formula:

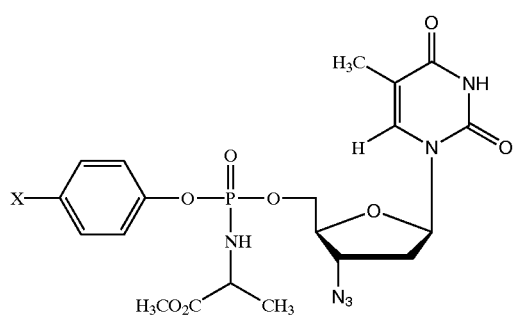
wherein
X is selected from Br and Cl;
or a pharmaceutically acceptable salt or ester thereof; and
a pharmaceutically acceptable carrier, adjuvant or diluent.
17. The composition of claim 15, wherein X is Br.
18. The composition of claim 15, wherein X is Cl.
19. The composition of claim 15, wherein the virus comprises HIV.
* * * * *

UNITED STATES PATENT AND TRADEMARK OFFICE
CERTIFICATE OF CORRECTION

PATENT NO. : 6,528,495 B1  Page 1 of 3
DATED : March 4, 2003
INVENTOR(S) : Uckun et al.

It is certified that error appears in the above-identified patent and that said Letters Patent is hereby corrected as shown below:

Column 1,
Line 21, "dideoynucleoside" should read -- dideoxynucleoside --

Column 8,
Lines 26-58,

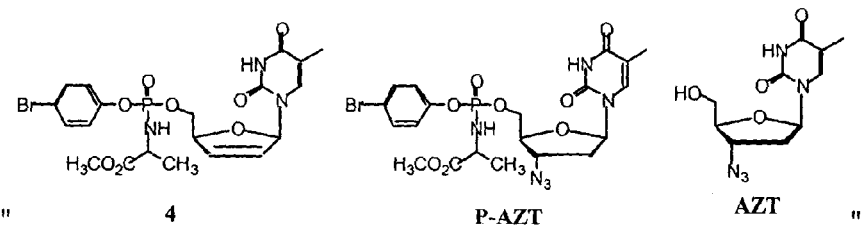

should read

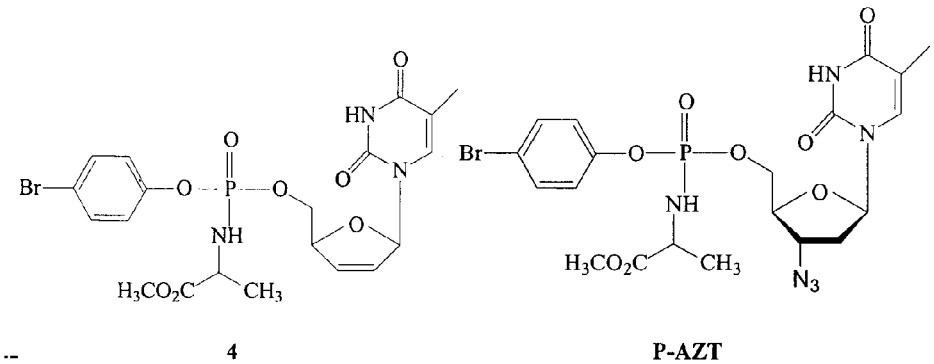

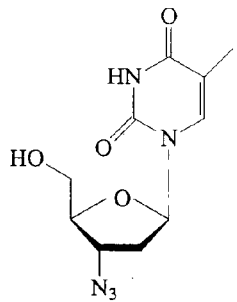

AZT --

UNITED STATES PATENT AND TRADEMARK OFFICE
CERTIFICATE OF CORRECTION

PATENT NO. : 6,528,495 B1
DATED : March 4, 2003
INVENTOR(S) : Uckun et al.

It is certified that error appears in the above-identified patent and that said Letters Patent is hereby corrected as shown below:

Column 13,
Line 31, "charaterization" should read -- characterization --

Column 20,
Lines 7-41, Table 4,

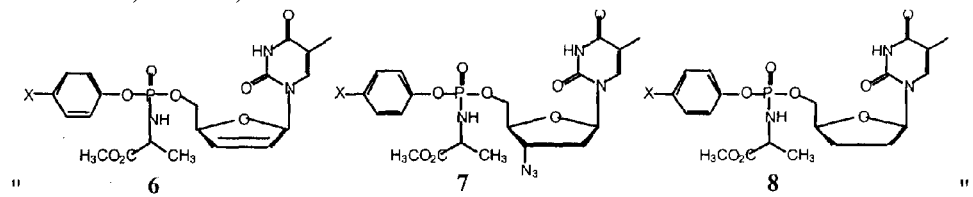

should read

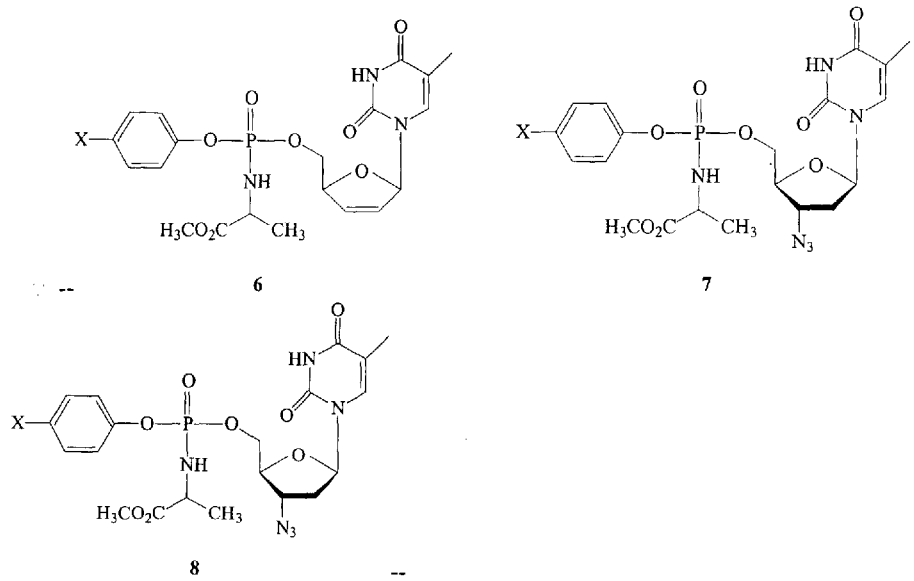

Column 21,
Lines 8-44, Table 5,

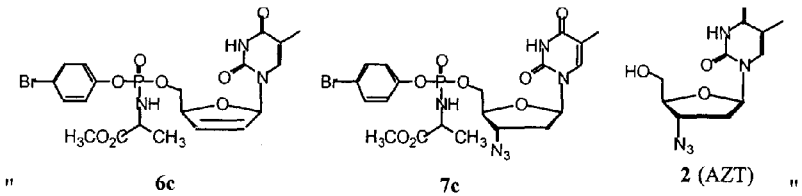

UNITED STATES PATENT AND TRADEMARK OFFICE
CERTIFICATE OF CORRECTION

PATENT NO. : 6,528,495 B1  Page 3 of 3
DATED : March 4, 2003
INVENTOR(S) : Uckun et al.

It is certified that error appears in the above-identified patent and that said Letters Patent is hereby corrected as shown below:

Column 21 (cont'd)
should read

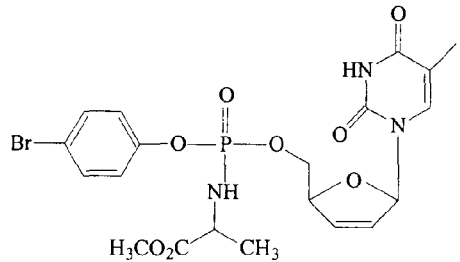

6c

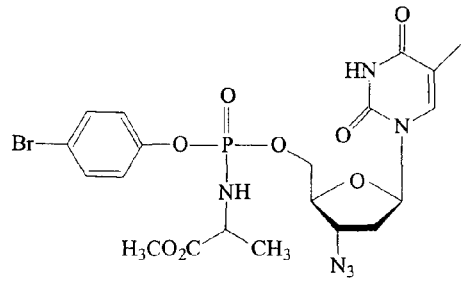

7c

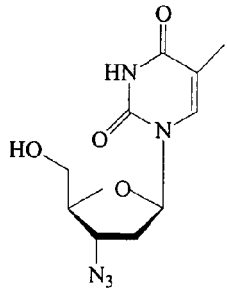

2 (AZT) --

Signed and Sealed this

Second Day of September, 2003

JAMES E. ROGAN
*Director of the United States Patent and Trademark Office*